(12) United States Patent
Kristiansen et al.

(10) Patent No.: US 8,496,913 B2
(45) Date of Patent: Jul. 30, 2013

(54) COMPRESSED CHEWING GUM TABLET

(75) Inventors: Tove Nordestgaard Kristiansen, Jelling (DK); Lars Gyldenvang, Gjerrild Mark (DK); Rikke Mikkelsen, Vejle (DK)

(73) Assignee: Gumlink A/S, Vejle (DK)

( * ) Notice: Subject to any disclaimer, the term of this patent is extended or adjusted under 35 U.S.C. 154(b) by 0 days.

(21) Appl. No.: 11/814,335

(22) PCT Filed: Jan. 27, 2006

(86) PCT No.: PCT/DK2006/000044
§ 371 (c)(1),
(2), (4) Date: Nov. 2, 2007

(87) PCT Pub. No.: WO2006/079343
PCT Pub. Date: Aug. 3, 2006

(65) Prior Publication Data
US 2008/0131379 A1 Jun. 5, 2008

(30) Foreign Application Priority Data

Jan. 28, 2005 (EP) ..................................... 05388005
Jan. 28, 2005 (EP) ..................................... 05388007

(51) Int. Cl.
*A61K 9/58* (2006.01)
(52) U.S. Cl.
USPC .......................................... 424/48; 433/216
(58) Field of Classification Search
USPC ............................................................ 426/3
See application file for complete search history.

(56) References Cited

U.S. PATENT DOCUMENTS

| 5,380,530 | A | 1/1995 | Hill et al. |
| 5,824,291 | A | 10/1998 | Howard et al. |
| 6,235,318 | B1 | 5/2001 | Lombardy, Jr. et al. |
| 7,232,581 | B2 * | 6/2007 | Mikkelsen et al. ............... 426/2 |
| 2001/0047009 | A1 | 11/2001 | Barabolak et al. |

FOREIGN PATENT DOCUMENTS

| DE | 28 08 160 A1 | 8/1979 |
| EP | 1 072 254 A1 | 1/2001 |
| EP | 1 449 525 A1 | 8/2004 |
| EP | 1 474 993 A1 | 11/2004 |
| WO | 00/42861 A1 | 7/2000 |
| WO | 03/039503 A1 | 5/2003 |
| WO | WO2004068965 | * 8/2004 |

OTHER PUBLICATIONS

Gaby, A., Xylitol Chewing Gum for prevention of caries, Towsend Letter for Doctors and Patients, 2004, p. 1-3.*

* cited by examiner

*Primary Examiner* — Frederick Krass
*Assistant Examiner* — Michael P Cohen
(74) *Attorney, Agent, or Firm* — Sughrue Mion, PLLC

(57) ABSTRACT

The present invention relates to a compressed chewing gum tablet possessing tooth brush properties, which compressed chewing gum tablet comprises at least gum base and a) at least one whitening agent, b) at least one fresh-breath agent, c) at least one anti-plaque agent, d) at least one anti-gingivitis agent, e) at least one re-mineralization agent, and f) optionally at least one anti-calculus agent, wherein the compressed chewing gum tablet at least partly is manufactured from a compressed mixture of granules and agents.

27 Claims, 1 Drawing Sheet

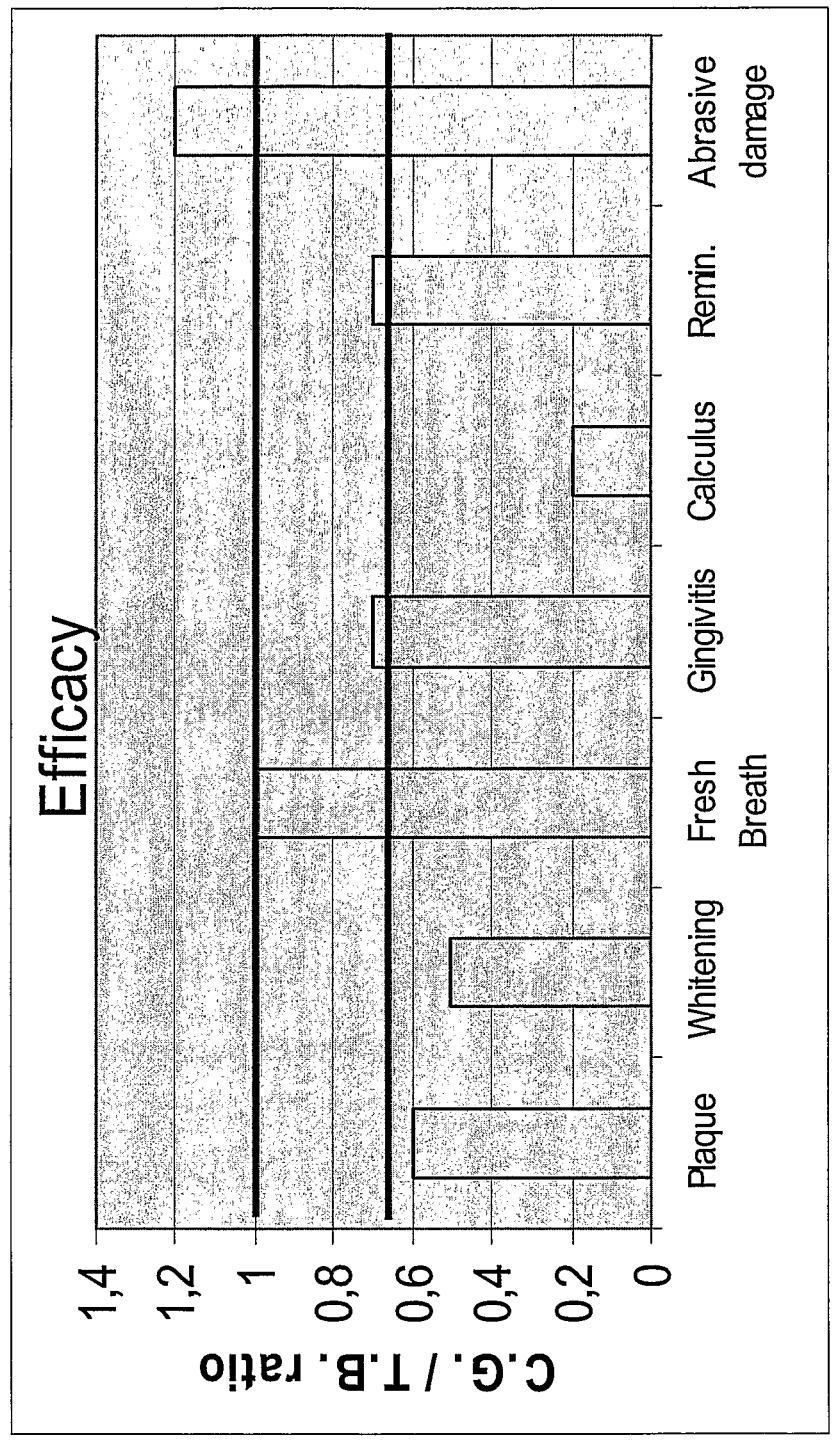

COMPRESSED CHEWING GUM TABLET

The present invention relates to a chewing gum tablet possessing tooth cleaning effects.

Chewing gum suitable for temporary cleaning of teeth is well-known. Such chewing gum is e.g. disclosed in the patent documents U.S. Pat. Nos. 5,380,530, 5,693,334, 6,365,130 B1 and US 2004/0115247 A1. However, the known types of chewing gum have hitherto only been capable to demonstrate a limited capacity for tooth cleaning for single day use or at the most a few days' use when a toothbrush is accidentally not available, after which period a thorough cleaning with toothbrush and toothpaste has been required, or for use as a supplement to daily cleaning with a toothbrush and toothpaste.

Brushing of teeth with a toothbrush is, however, rather rough on the teeth and especially on the gingiva and will eventually unavoidably lead to abrasive damage on the treated teeth or on the gums.

For several decades a dogma has existed among professionals and also in general among adults and particularly among parents that the sole method of properly cleaning teeth is daily use of toothbrush and toothpaste.

Most people experience from time to time that a toothbrush is unavailable and then have to resort to using other means, such as a chewing gum, mouth wash or lozenges, in order to at least obtain a sensation of fresh breath. But they are clearly aware that this does not account to proper tooth cleaning. People continue to brush teeth daily even when they experience brushing damages. They will sometimes change to use toothbrushes having softer bristles or use electrical toothbrushes in order to obtain more favourable brush movements over the teeth and gingiva surfaces, but they do not dispense with tooth brushing as such.

An object of the present invention is to provide a dental care product for daily use, which dental care product renders use of toothbrush and toothpaste superfluous.

Thus, the present invention relates to a compressed chewing gum tablet possessing tooth brush properties, which compressed chewing gum tablet comprises at least gum base and:
  a) at least one whitening agent,
  b) at least one fresh-breath agent,
  c) at least one anti-plaque agent,
  d) at least one anti-gingivitis agent,
  e) at least one re-mineralization agent, and
  f) optionally at least one anti-calculus agent, wherein said compressed chewing gum tablet at least partly is manufactured from a compressed mixture of granules and agents.

The present invention provides surprisingly a compressed chewing gum tablet in the form of a dental care product having teeth cleaning properties making teeth cleaning with toothbrush and toothpaste superfluous, and without the highly undesired effect of causing abrasive damage on the teeth and gingiva.

By using gum base included in granules it is possible to provide a basis for a dental care product having excellent properties in respect of avoiding abrasive damage on teeth. However, gum base alone does not have sufficient cleaning effect to ensure an effective daily cleaning of teeth and there is a need for adding a number of active ingredients to the gum base. It has been found that at least one agent with whitening effect, at least one agent with fresh-breath effect, at least one agent with anti-plaque effect, at least one agent with anti-gingivitis effect, at least one agent with re-mineralization effect and optionally at least one agent with anti-calculus effect are required in order to produce a toothbrush substitute with a cleaning effect which makes it possible to avoid the use of a toothbrush and yet maintain the teeth and gingiva in well cleaned condition. It is a major benefit by dispensing with the use of a toothbrush that the abrasive damages caused by brushing teeth are avoided.

As the skilled person would realise, the desired dental care effects are mainly provided by anti-plaque agents, anti-gingivitis agents, anti-calculus agents, and/or re-mineralization agents, respectively.

The whitening and fresh breath ingredients serve to improve the feeling of cleanness and freshness in the mouth subsequent to use of the toothbrush substitute according to the invention. The use of gum granules in a compressed chewing gum tablet has made it possible to manufacture a dental care product where optional undesired reactions during manufacture and storage (or reactions that should not take place before the compressed chewing gum tablet is chewed) between the different agents can be avoided. The use of gum granules makes it possible to keep different agents apart. One agent may be present in the gum granules optionally incorporated in the gum base. Another ingredient may be present in the tablet in the space between the compressed granules or optionally in a coating. Alternatively gum granules with different agents can be used. For example a first fraction of the gum granules may comprise at least one agent, and a second fraction of the gum may comprise at least one agent and at least one agent comprised in the first fraction is different from at least one agent comprised in the second fraction.

Moreover, the compressed chewing gum tablet may comprise two or more layers. In such an embodiment of the invention different agents may be present in different layers.

One example of agents where undesired reaction may occur is osteopontin (anti-gingivitis agent) and zinc salts (anti-plaque agent).

Contrary to conventional thinking, the present inventors have unexpectedly found that it is possible to provide a dental care product based on gum base that is capable of cleaning teeth with an efficiency that is overall comparable to cleaning teeth with toothbrush and toothpaste. Use of a toothbrush might to some degree be more effective in certain of the desirable effects than the effects of using the present dental care product, but this is outbalanced by avoiding the undesired effect of abrasive damage on the teeth and gingiva.

Furthermore, it has also appeared that the dental care product according to the invention is much easier and more convenient in use than the conventional toothbrush with toothpaste. This is in particular advantageously in case of children and disabled persons to whom handling of a toothbrush can be extremely difficult, which fact may very easily lead to the effect that the teeth cleaning become ineffective.

The availability of the present dental care product is much higher than for a toothbrush, because the compressed chewing gum tablet will normally be carried with or on the user, whereas a toothbrush is kept in the bathroom. The dental care product according to the invention can be used anywhere at any time, as there is no need for access to water, like e.g. in a bathroom. Consequently, the dental care product according to the invention can be used when driving a car, during work, while watching television etc., thereby providing much more freedom to the user.

The individual pieces of compressed chewing gum tablets will typically be used for longer duration than the time spent on brushing teeth. When a toothbrush is used the recommended duration of brushing is 2 minutes in Europe and 1 minute in the US, but many persons spend less time than that. After completed brushing of teeth it is common to rinse the mouth with water, and in doing so the active substances in the toothpaste are washed out from the mouth. However, when using the chewing gum according to the present invention, chewing is much more prolonged and the mouth is exposed to the active ingredients for longer time during the chewing. In addition the user will typically not rinse the mouth with water after completed chewing, and thus the active agents released during chewing will remain in the mouth, especially in the confined areas near the gingiva facing towards the chins where the need for a cleaning effect is the most pronounced. It is also a benefit of the present invention that the active ingredients will automatically spread to all surfaces in the mouth, whereas a toothbrush is only really effective in the areas that are actually brushed by the action of the user.

Preferably, the agents are provided in an amount sufficient for constituting the daily dental care. That the agents are provided in an amount sufficient for daily dental care means that they are released from the compressed chewing gum tablet in an amount sufficient to provide the desired effect on the teeth and oral cavity.

In a preferred embodiment of the compressed chewing gum tablet according to the invention the chewing gum is layered. The chewing gum may comprise two or three or more layers. The layers may be placed on top of each other or side by side. Optionally the layers have different colours.

When the chewing gum is layered it is possible to provide embodiments wherein different agents are present in different layers in the chewing gum. This is particularly advantageous when the different agents interact. When the agents are present in different layers undesired reactions between such agents can be avoided until the reaction is needed and desired.

Thus, it is possible to provide a compressed chewing gum tablet wherein at least one of the agents a) to f) is present in the chewing gum in only one of the layers.

Moreover, a compressed chewing gum tablet can be provided, wherein two or more of the layers include agents that are not present in all layers in the chewing gum.

The invention also encompasses an embodiment, in which the chewing gum comprises at least one barrier layer. A barrier layer may serve to separate two active agents that will react when mixed. Optionally the barrier layer is a layer in a layered tablet e.g. a chewing gum tablet comprising three or more layers.

For some embodiments of the toothbrush substitute it is preferred that the chewing gum is coated. A coating may protect the active agents from decomposition e.g. caused by oxygen. Moreover, a coating may contribute to maintain a desired moisture content in the chewing gum. The coating may be a hard coating and/or a film coating.

The coating itself can also include one or more of the active ingredients. Accordingly, in an embodiment of the chewing gum, at least one anti-plaque, anti-gingivitis, remineralization or anti-calculus agent and/or at least one whitening or fresh-breath agent. Such an embodiment may for instance be advantageous when a rapid release of active agents is desirable.

In an embodiment of the invention the compressed chewing gum tablet is coated with an outer coating. Preferably the outer coating is a hard coating.

In a preferred embodiment of the invention the hard coating is a coating selected from the group consisting of a sugar coating and a sugarless coating and a combination thereof.

In a further embodiment of the invention the hard coating comprises 50 to 100% by weight of a polyol typically selected from the group consisting of sorbitol, maltitol, mannitol, xylitol, erythritol, lactitol and isomalt.

In an alternative embodiment of the invention the outer coating is an edible film comprising at least one component selected from the group consisting of an edible film-forming agent and a wax. In a preferred embodiment of the invention the film-forming agent is selected from the group consisting of a cellulose derivative, a modified starch, a dextrin, gelatine, shellac, gum arabic, zein, a vegetable gum, a synthetic polymer and any combination thereof.

In an embodiment of the invention the outer coating comprises at least one additive component selected from the group consisting of a binding agent, a moisture absorbing component, a film forming agent, a dispersing agent, an antisticking component, a bulking agent, a flavouring agent, a colouring agent, a pharmaceutically or cosmetically active component, a lipid component, a wax component, a sugar, an acid and an agent capable of accelerating the after-chewing degradation of the degradable polymer.

In an embodiment of the invention the outer coating is a soft coating.

In an embodiment of the invention the soft coating comprises a sugar free coating agent.

The invention also provides for a compressed chewing gum tablet, wherein at least one of the agents a) to f) is present in the coating.

Furthermore, in an alternative preferred embodiment at least one of the agents a) to f) is present only in some of the gum granules, and at least another of the agents a) to f) is present only in other of the gum granules prior to compressing the granules into chewing gum tablets. The embodiment is suitable for preventing undesired reactions between different agent during manufacture and storage.

In a preferred embodiment the compressed chewing gum tablet comprises one or more chewing gum ingredients selected from sweeteners, high-potent sweeteners and/or flavour in order to provide a pleasant taste.

As regular use of a conventional toothbrush eventually leads to abrasive damages it is for some embodiments preferred that the compressed chewing gum tablet is substantially free of abrasives.

It is preferred that the gum base constitutes at least 35 weight-%, more preferably the gum base constitutes at least 37 weight-%, even more preferably at least 39 weight-% of the compressed chewing gum tablet. A high content of gum base provides for better organoleptic properties of the compressed chewing gum tablet.

For the purpose of obtaining the best possible properties of the compressed chewing gum tablet according to the invention it is desired that the gum base constitutes 60-100% of the granules, preferably the gum base constitutes 70-100% of the granules, more preferably the gum base constitutes 85-100% of the gum granules. In a preferred embodiment the granules are constituted by gum base (pure gum base). The granules comprising gum base is also referred to as gum granules.

Although the agents may be present in the compressed chewing gum tablet in the space between the gum granules, in a preferred embodiment of the compressed chewing gum tablet according to the invention at least one of the agents is present in the gum granules and mixed into the gum base. In such a manner it is possible to separate reactive agents from other agents.

The invention also relates to use of a compressed chewing gum tablet according to the invention as a tooth brush substitute for avoiding the risk of tooth and gingiva damage inherent in tooth brushing by maintaining such oral hygiene by chewing the compressed chewing gum tablets that no need for brushing exists.

Preferably the use of the compressed chewing gum tablet when chewed on a daily basis as a toothbrush substitute provides a) a whitening effect corresponding to at least 50% of the whitening effect of daily brushing of teeth with a new toothbrush, b) a fresh-breath effect corresponding to at least 100% of the fresh-breath effect of daily brushing of teeth with a new toothbrush, c) an anti-plaque effect corresponding to at least 60% of the anti-plaque effect of daily brushing of teeth with a new toothbrush, d) an anti-gingivitis effect corresponding to at least 65% of the anti-gingivitis effect of daily brushing of teeth with a new toothbrush, e) optionally a re-mineralization effect corresponding to at least 65% of the re-mineralization effect of daily brushing of teeth with a new toothbrush, f) optionally an anti-calculus effect corresponding to at least 25% of the anti-calculus effect of daily brushing of teeth with a new toothbrush, and providing a substantially lower abrasive effect than the abrasive effect caused by daily brushing of teeth with a new toothbrush.

A suitable whitening effect corresponds to at least 65%, more preferred at least 85%, and even more preferred at least 100%, of the whitening effect of daily brushing of teeth with a new toothbrush.

A suitable anti-plaque effect corresponds to at least 65%, more preferred at least 85%, and even more preferred at least 100%, of the anti-plague effect of daily brushing of teeth with a new toothbrush.

A suitable anti-gingivitis effect corresponds to at least 75%, more preferred at least 85%, and even more preferred at least 100%, of the anti-gingivitis effect of daily brushing of teeth with a new toothbrush.

A suitable re-mineralization effect corresponds to at least 75%, more preferred at least 85%, and even more preferred at least 100%, of the re-mineralization effect of daily brushing of teeth with a new toothbrush.

A suitable anti-calculus effect corresponds to at least 50%, more preferred at least 65%, and even more preferred at least 100%, of the anti-calculus effect of daily brushing of teeth with a new toothbrush.

In a preferred embodiment of the use of the compressed chewing gum tablet according to the invention, pieces of the compressed chewing gum tablet are intended for chewing one, two, three, four five or more times per day, and preferably after eating.

Moreover, the individual pieces of the compressed chewing gum tablet is intended for chewing for about 5 to about 20 minutes.

The invention also relates to the compressed chewing gum tablet for use as a toothbrush substitute.

The chewing gum according to the invention can in one embodiment be substantially free of abrasives. However, the chewing gum preferably contains some amount of abrasive and polishing agents, in particular of a type softer than dental enamel and dentine. As such abrasives and polishing agents are included in the chewing gum they will act only on the outer portions of the teeth where they cannot cause an abrasive effect on the teeth because the enamel is strong. And the chewing gum cannot press down gingiva and any abrasive or polishing agents present in the chewing gum cannot act on the vulnerable innermost portions of the teeth.

The toothbrush abrasive effect is in the present context understood as the brushing effect causing abrasive damage on gingiva and the teeth side surfaces. The mechanism involved in development of these damages is understood in the following manner. During the brushing of teeth with a toothbrush, the toothbrush bristles push against the gingiva and cause exposure of the innermost portion of the tooth side surface. This portion of the tooth side surface normally lies well protected behind gingival tissue. This portion is weak in a mechanical sense because the enamel is thin or even missing in this portion. By the brushing the toothbrush bristles act abrading on this weak portion of the tooth side surface. The bristles also penetrate in between the gingiva and said weak portion of the tooth and can cause abrasive damage on the gingival tissue so that gingiva over time is worn down with the result that said weak portion is permanently exposed. With respect to the outer portion of the tooth the enamel is here so thick and strong that the toothbrush cannot in the outer portion really act with an abrasive effect in the sense of the present description.

By the term "whitening agents" as used herein is meant any agent, which is able to modify the colour of the teeth or to remove or bleach intrinsic or extrinsic stains on or in tooth surfaces for example by oxidising organic pigments or chromogens in the tooth.

The whitening agents are conveniently selected from teeth colour modifying substances that may be considered among the oral care actives useful in the chewing gum according to the invention. These substances are suitable for modifying the colour of the teeth in order to satisfy the consumer. Examples of such whitening agents are those listed in the CTFA Cosmetic Ingredient Handbook, 3.sup.rd Edition, Cosmetic and Fragrances Association Inc., Washington D.C. (1982), which are incorporated herein by reference. Specific examples include talc, mica, magnesium carbonate, calcium carbonate, calcium pyrophosphate, baking soda, Icelandic moss, bamboo, sodium hexametaphosphate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Typical levels are from about 0.05% to about 20%, preferably from about 0.1% to about 15% and most preferably from about 0.25% to about 10%, by weight, of the composition.

Whitening agents for use herein may also comprise materials that remove or bleach intrinsic or extrinsic stains on or in tooth surfaces. Examples of such whitening agents are peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Suitable metal chlorites include calcium chlorite, barium chlorite, magnesium chlorite, lithium chlorite, sodium chlorite and potassium chlorite. As additional bleaching substances hypochlorite, and chlorine dioxide may be mentioned. A preferred percarbonate is sodium percarbonate. Preferred persulphates are oxones. The content of these substances is dependent on the available oxygen or chlorine. The content of these ingredients in the chewing gum according to the invention is generally in the range from about 0.1% to about 35%, preferably from about 1% to about 25% and most preferably from about 5% to about 10%, by weight of the chewing gum.

In a preferred embodiment the whitening agent is selected from the group consisting of baking soda, Icelandic moss, Icelandic moss extract, bamboo, bamboo extract, calcium pyrophosphate, calcium carbonate, sodium hexa-metaphosphate, nature identical substitutes thereof, and mixtures thereof.

In another embodiment whitening agents are selected from the group consisting of baking soda, Icelandic moss, bamboo, calcium pyrophosphate, calcium carbonate, and sodium hexa-metaphosphate.

In the most preferred embodiment the whitening agent are selected from $NaHCO_3$, calcium carbonate, calcium pyrophosphate, titandioxid, and sodium hexa-metaphosphate.

By the term "fresh-breath agents" as used herein is meant any agent, which is able to control mouth-odor-causing bacteria, as for example agents which are able to control hydrogen sulphide-forming bacteria, as well as any agent which is able to absorb, adsorb, bind or otherwise complex the volatile oral malodour materials.

The fresh-breath agents are preferably selected from agents for oral malodour control, which include a wide variety of materials. Suitable in the chewing gum according to the invention are anti-microbial agents. Such agents may include 5-chloro-2-(2,4-dichlorophenoxy)-phenol, commonly referred to as triclosan, and described in the Merck Index, 11$^{th}$ Edition, (1989), pp 1529 (entry No. 9573) in U.S. Pat. No. 3,506,720, and in European Patent publication No. 0 251 591, phthalic acid and its salts including, but not limited to those disclosed in U.S. Pat. No. 4,994,262, preferably magnesium mono-potassium phthalate, chlorohexidine (Merck Index, No. 2090), alexidine (Merck Index, No. 222), hexetidine (Merck Index, No. 4624), sanguinarine (Merck Index, No. 8320), benzalkonium chloride (Merck Index, No. 1066), salicylanilide (Merck Index, No. 8299), domiphen bromide (Merck Index, No. 3411), cetylpyridinium chloride (CPC) (Merck Index, No. 2024), tetradecylpyridinium chloride (TPC), N-tetradecyl-4-ethylpyridinium chloride (TDEPC), octenifine, delmopinol, octapinol, and other piperidine derivatives, nicin preparations, zinc/stannous ion agents, antibiotics, such as augmentin, amoxicilline, tetracycline, doxycycline, hexadine, minocycline, and metronidazole, and analogues and salts of the above, methyl salicyclate, and mixtures of any of the above.

Illustrative zinc sources in the form of compounds with fresh breath properties for use as fresh-breath agents are zinc oxide, zinc silicate, zinc carbonate, zinc acetate, zinc phosphate, zinc stannate, zinc tetrafluoroborate, zinc hexafluorosilicate, zinc citrate, zinc benzoate, zinc oxalate, zinc stearate, zinc chloride, zinc sulfate, zinc nitrate, zinc phenolsulfonate, zinc carboxymethylsuccinate, and the like. The zinc compounds may also be present as a complex, with a complexing agent such as polyethylenimine or ethylenediamine tetraacetic acid.

A further group of natural extracts which are useful for their oral malodour control benefits include extracts obtained from the tea (green tea, red tea, white tea and black tea), honey suckle, coriander, thyme, propolis, tea tree oil, barberry bark, Champex®, sunphenon, applephenon, gold thread, magnolia plants or mixtures thereof. It is preferred that chewing gum according to the present invention comprise from about 0.01% to about 5%.

Extracts suitable for use in the present invention can be obtained from any part of the plant including the leaf, stem, bark, pulp, seed, flesh, juice, root and mixtures thereof. In the context of the present invention the term "extract" is intended to encompass infusions, liquid extracts, liquid concentrates of extracts, fractionated extracts and powdered extracts of the plants/berries/fruits etc. Extracts may be obtained by any conventional technique, such as water extraction, ethanol extraction or methanol extraction where appropriate. It is within the standard procedure of a skilled person to perform an appropriate extraction procedure in order to obtain an extract comprising the beneficial substances extracted from the plants, berries or fruits for use in the present invention.

By the term "nature identical substitute" as used herein is meant any natural or artificial compound or combination of compounds, which has a chemical structure identical to that found in nature. Most often a nature identical substitute is found as the main functional component of an extract or as a mixture of two or more of the main functional components in an extract. By the term "functional component" as used herein is meant the component performing the function of whitening the teeth, when mentioned in connection with whitening agents, or performing the function of providing the fresh-breath, when mentioned in connection with fresh-breath agents, etc. No nature identical substitutes can be found for inorganic compounds. The nature identical substitute may be prepared by use of chemical synthesis, by chemical modification of a compound of natural origin or by use of any enzymatical reaction pathway. The term is well known within the art and, therefore, a skilled person will appreciate whether an agent mentioned may or may not be found as a nature identical substitute.

The following essential oils are also known to have anti-microbial activity and are therefore optionally used in the chewing gum according to the present invention. By the term "essential oil" as used herein is meant any oil that impart the characteristic odors of plants. Oils, which are suitable for use in the present invention, include thymol, geraniol, carvacrol, hinokitiol, eucalyptol, catechol (particularly 4-allyl catechol), and mixtures thereof.

Another class of oral malodour control agents include absorbents. These are used to absorb, adsorb, bind or otherwise complex the volatile oral malodour materials. Examples of such agents include talc, mushroom extract, zeolite, cyclodextrin, silica shell and mixtures thereof. Such materials are preferably used in a range from about 0.5% to about 10%, preferably from about 1% to about 5%, by weight of the chewing gum.

In a preferred embodiment the fresh-breath agent is selected from the group consisting of a zinc source, coriander, coriander extract, green tea, green tea extract, propolis, propolis extract, tea tree oil, barberry bark, barberry bark extract, hexetidine, champes, sunphenol, applephenol, red tea, red tea extract, white tea extract, thyme extract, and mixtures thereof.

In another embodiment fresh-breath agents are selected from the group consisting of zinc acetate, coriander, green tea, propolis, tea tree oil, barberry bark, hexetidine, champes, sunphenol, applephenol, red tea, green tea extract, white tea and thyme extract.

In the most preferred embodiment the fresh-breath agents are selected from the group consisting of green tea extract, zinc acetate, 2-isopropyl-5-methyl-phenol (thymol), and eucalyptus.

Plaque is defined as a bacteria-containing substance that adhere to the surfaces of the teeth as well as on other surfaces of the oral cavity. Hence, by the term "anti-plaque agents" as used herein is meant any agent, which is able to prevent or inhibit the formation and accumulation of bacterial deposits on the surfaces of the oral cavity or to degrade or remove existing bacterial deposits on the surfaces of the oral cavity.

Examples of anti-plaque agents include xylitol and other anti-microbial agents. The inhibition effects of the xylitol on oral microbes may have better effect when used in conjunction with an extract since the extract is also acting to disable the microbes. Anti-plaque agents include fluoride ion sources.

Typical examples of active ingredients that are particularly desirable from considerations of anti-plaque effectiveness, safety and formulation include: naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, betalactamase inhibitors; meziocillin, piperacillin, aztreonam, norfloxacin, trimethoprim, ceftazidime, dapsone; halogenated diphenyl ethers, e.g. 2',4,4'-trichloro-2-hydroxydiphenyl ether (Triclosan), 2,2'-dihydroxy-5,5'-dibromo-diphenyl ether; halogenated salicylanilides, e.g. 4',5-dibromosalicylanilide, 3,4',5-trichlorosalicylanilide, 3,4',5-tribromosalicylanilide, 2,3,3',5-tetrachloro-salicylanilide, 3,3,3',5-tetrachlorosalicylanilide, 3,5-dibromo-3'-trifluoromethyl-salicylanilide, 5-n-octanoyl-3'-trifluoromethyl-salicylanilide, 3,5-dibromo-4'-trifluoromethyl-salicylanilide, 3,5-dibromo-3'-trifluoromethyl-salicylanilide (Fluorophene); benzoic esters, e.g. methyl-p-hydroxybenzoic ester, ethyl-p-hydroxybenzoic ester, propyl-p-hydroxybenzoic ester, butyl-p-hydroxybenzoic ester; halogenated carbanilides, e.g. 3,4,4'-trichlorocarbanilide, 3-trifluoromethyl-4,4'-dichlorocarbanilide, or 3,3,4'-trichlorocarbanilide; phenolic compounds (including phenol and its homologs, mono- and poly-alkyl and aromatic halo-phenol and their homologs), e.g. phenol, 2-methyl-phenol, 3-methyl-phenol, 4-methyl-phenol, 4-ethyl-phenol, 2,4-dimethyl-phenol, 2,5-dimethyl-phenol, 3,4-dimethyl-phenol, 2,6-dimethyl-phenol, 4-n-propyl-phenol, 4-n-butyl-phenol, 4-n-amyl-phenol, 4-tert-amyl-phenol, 4-n-hexyl-phenol, 4-n-heptyl-phenol, 2-methoxy-4-(2-propenyl)-phenol (Eugenol), 2-isopropyl-5-methyl-phenol (Thymol), mono- and poly-alkyl- and aralkyl-halophenols, methyl-p-chlorophenol, ethyl-p-chlorophenol, n-propyl-p-chlorophenol, n-butyl-p-chlorophenol, n-amyl-p-chlorophenol, sec-amyl-p-chlorophenol, n-hexyl-p-chlorophenol, cyclohexyl-p-chlorophenol, n-heptyl-p-chlorophenol, n-octyl-p-chlorophenol, o-chlorophenol, methyl-o-chlorophenol, ethyl-o-chlorophenol, n-propyl-o-chlorophenol, n-butyl-o-chlorophenol, n-amyl-o-chlorophenol, tert-amyl-o-chlorophenol, n-hexyl-o-chlorophenol, n-heptyl-o-chlorophenol, p-chlorophenol, o-benzyl-p-chlorophenol, o-benzyl-m-methyl-p-chlorophenol, o-benzyl-m,m-dimethyl-p-chlorophenol, o-phenylethyl-p-chlorophenol, o-phenylethyl-m-methyl-p-chlorophenol, 3-methyl-p-chlorophenol, 3,5-dimethyl-p-chlorophenol, 6-ethyl-3-methyl-p-chlorophenol, 6-n-propyl-3-methyl-p-chlorophenol, 6-iso-propyl-3-methyl-p-chlorophenol, 2-ethyl-3,5-dimethyl-p-chlorophenol, 6-sec-butyl-3-methyl-p-chlorophenol, 2-iso-propyl-3,5-dimethyl-p-chlorophenol, 6-diethylmethyl-3-methyl-p-chlorophenol, 6-iso-propyl-2-ethyl-3-methyl-p-chlorophenol, 2-sec-amyl-3,5-dimethyl-p-chlorophenol, 2-diethylmethyl-3,5-dimethyl-p-chlorophenol, 6-sec-octyl-3-methyl-p-chlorophenol, p-bromophenol, methyl-p-bromophenol, ethyl-p-bromophenol, n-propyl-p-bromophenol, n-butyl-p-bromophenol, n-amyl-p-bromophenol, sec-amyl-p-bromophenol, n-hexyl-p-bromophenol, cyclohexyl-p-bromophenol, o-bromophenol, tert-amyl-o-bromophenol, n-hexyl-o-bromophenol, n-propyl-m,m-dimethyl-o-bromophenol, 2-phenyl-phenol, 4-chloro-2-methyl-phenol, 4-chloro-3-methyl-phenol, 4-chloro-3,5-dimethyl-phenol, 2,4-dichloro-3,5-dimethyl-phenol, 3,4,5,6-tetrabromo-2-methylphenol, 5-methyl-2-pentylphenol, 4-isopropyl-3-methylphenol, 5-chloro-2-hydroxydiphenyl-methane; resorcinol and its derivatives, e.g. resorcinol, methylresorcinol, ethyl-resorcinol, n-propyl-resorcinol, n-butyl-resorcinol, n-amyl-resorcinol, n-hexyl-resorcinol, n-heptyl-resorcinol, n-octyl-resorcinol, n-nonyl-resorcinol, phenyl-resorcinol, benzyl-resorcinol, phenylethyl-resorcinol, phenylpropyl-resorcinol, p-chlorobenzyl-resorcinol, 5-chloro-2,4-dihydroxydiphenyl-methane, 4'-chloro-2,4-dihydroxydiphenyl-methane, 5-bromo-2,4-dihydroxydiphenyl-methane, 4''-bromo-2,4-dihydroxydiphenyl-methane; and bisphenolic compounds, e.g. bisphenol A, 2,2'-methylene-bis-(4-chlorophenol), 2,2'-methylene-bis-(3,4,6-trichlorophenol) (hexachlorophene), 2,2'-methylene-bis-(4-chloro-6-bromophenol), bis-(2-hydroxy-3,5-dichlorophenyl)-sulfide, and bis-(2-hydroxy-5-chlorobenzyl)-sulfide.

Illustrative of polyphosphate compounds with plaque-inhibiting properties are dialkali metal and tetraalkali metal pyrophosphate and mixtures thereof in a hydrated or unhydrated form. Illustrative of pyrophosphate salts are $Na_2H_2P_2O_7$, $Na_4P_2O_7$ and $K_4P_2O_7$. Other suitable polyphosphates include hydrated or unhydrated alkali metal tripolyphosphates such as $Na_5P_3O_{10}$ and $K_5P_3O_{10}$.

Plaque buffers such as urea, calcium lactate, calcium glycerophosphate and strontium polyacrylates, ammonium carbonate and vitamins such as Vitamins A, C and E are also included.

Nutraceuticals and nutritional supplements may also be added to chewing gums as active agents against plaque. Among these are herbs and botanicals that include, but are not limited to chamomile, *echinacea, Eucalyptus* and green tea.

Metal cations can also be used as anti-bacterial and anti-plaque agents. The metal cations are selected from the metals of Group 5 (V, Nb, Ta); Group 6 (Cr, Mo, W); Group 7 (Mn, Tc, Re); Group 8 (Fe, Ru, Os); Group 9 (Co, Rh, Ir); Group 10 (Ni, Pd, Pt); Group 11 (Cu, Ag, Au); Group 12 (Zn, Cd, Hg); Group 14 (Ge, Sn, Pb); Group 16 (Se, Te, PO); and mixtures thereof. Preferably the metal cation is selected from any monovalent or divalent cation selected from the group consisting of zinc, manganese, copper, iron, cobalt, silver, selenium, tin and vanadium; preferably from the group consisting of zinc, manganese, copper, iron, silver, and tin; more preferably from the group consisting of zinc, copper, silver and tin and most preferably from the group consisting of zinc and tin.

Illustrative of zinc compounds with plaque-inhibiting properties are zinc oxide, zinc silicate, zinc acetate, zinc carbonate, zinc phosphate, zinc stannate, zinc tetrafluoroborate, zinc hexafluorosilicate, zinc citrate, zinc benzoate, zinc oxalate, zinc stearate, zinc chloride, zinc sulfate, zinc nitrate, zinc phenolsulfonate, zinc carboxymethylsuccinate, and the like. The zinc compound also can be in the form of a complex, with a complexing reagent such as polyethylenimine or ethylenediamine tetraacetic acid.

A wide variety of metal cation salts are useful in the present invention. These include so called "water-insoluble salts" which have a solubility of less than about 0.5 g per 100 ml at 25° C. and "water soluble salts" which have a solubility of greater than or equal to about 0.5 g per 100 ml at 25° C. It is also possible to use mixtures of these salts. Such mixtures can have several advantages in the compositions of the present invention since they are likely to have different complexing properties with the polyphosphate anions. In addition they have different release rates in the saliva and can therefore act to provide controlled release profiles. Examples of salts that are suitable for use herein include acetate, ammonium sulphate, bromide, chloride, chromate, citrate, dithionate, fluorosilicate, tartrate, fluoride, formate, iodide, nitrate, phenol sulphate, salicyclate, sulphate, gluconate, succinate, glycerophosphate, lactate and mixtures thereof.

In a preferred embodiment the anti-plaque agent is selected from the group consisting of a zinc source, ammonium carbamate, eucalyptus, eucalyptus extract, cranberry, cranberry extract, xylitol, chlorhexidine, seaweed, seaweed extract, epigallocatechin gallate, osteopontin, baking soda, nature identical substitutes thereof, and mixtures thereof.

In another embodiment the anti-plaque agents are selected from the group consisting of zinc acetate, ammonium carbamate, eucalyptus, cranberry, xylitol, chlorhexidine, seaweed, osteopontin and baking soda.

In the most preferred embodiment the anti-plaque agents are selected from the group consisting of *aronia, eucalyptus*, immuglobuline-lysozyme (e.g. Ig-lyt or IG-LY 4023), xylitol, green tea extract, and zinc acetate.

Gingivitis is defined as an inflammation of the gums surrounding the teeth caused by a build up of plaque or food particles. Hence by the term "anti-gingivitis agents" as used herein is meant any agent, which is able to prevent or inhibit an inflammation of the gums surrounding the teeth caused by a build up of plaque or food particles.

Consequently, anti-gingivitis agents can be anti-inflammatory agents, such as salicylic acid derivatives (e.g. aspirin), paraminophenol derivative (e.g. acetaminophen), indole and indene acetic acids (indomethacin, sulindac and etodalac), heteroaryl acetic acids (tolmetin, diclofenac and ketorolac), aryl propionic acid derivatives (ibuprofen, naproxen, ketoprofen, fenopren, oxaprozine), anthranilic acids (mefenamic acid, meclofenamic acid), enolic acids (piroxicam, tenoxicam, phenylbutazone and oxyphenthatrazone), lactic acid bacteria (LAB), Osteopontin (ONP), Immuglobuline-lysozyme, hexefine, Aloe Vera, chlorhexedine, myrrh, or sage.

Examples of anti-gingivitis agents also include psychotherapeutic agents, such as thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, or eldepryl.

In a preferred embodiment the anti-gingivitis agent is selected from the group consisting of chlorhexidine, myrrh, myrrh extract, neem, neem extract, sage, sage extract, aloe vera, aloe vera extract, hexatidine, osteopontin, quince, quince extract, immuglobuline-lysozyme powder, nature identical substitutes thereof, and mixtures thereof. As an example of an immuglobuline-lysozyme powder, the powder sold under the tradename IG-LY 4023 (obtainable from Pedersen's Laboratorium, Vejle, Denmark) may be mentioned.

In another embodiment the anti-gingivitis agents are agents selected from the group consisting of chlorhexidine, myrrh, neem, sage, aloe vera, hexatidine, osteopontin, quince, and immuglobuline-lysozyme powder (Tradename IG-LY 4023, obtainable from Pedersen's Laboratorium, Vejle, Denmark).

In the most preferred embodiment the anti-gingivitis agents are agents selected from the group consisting of osteopontin and immuglobuline-lysozyme.

Re-mineralization is defined as the reversal of demineralisation of tooth enamel. Hence, by the term "re-mineralization agents" as used herein is meant any agent, which is able to build up the enamel as well as any agent, which is able to inhibit the demineralization of tooth enamel.

Examples of such re-mineralization agents include pH adjusting agents, which may also be added to make the composition safe for oral tissues. These pH adjusting agents, or buffers, can be any material that is suitable to adjust the pH of the composition. Suitable materials include sodium bicarbonate, sodium phosphate, sodium hydroxide, ammonium hydroxide, potassium hydroxide, sodium stannate, triethanolamine, citric acid, hydrochloric acid, sodium citrate, calcium, fluoride, Phoscal, dicalcium phosphate, Osteopontin (ONP), monosodium phosphate, trisodium phosphate, sodium hydroxide, sodium carbonate, pectin, benzocaine, analgesics, sanguinarine extract, metronidazole, strontium chloride, potassium nitrate, carrageenan, cough and cold remedies, and the like.

In a preferred embodiment the re-mineralization agent is selected from the group consisting of calcium fluoride, osteopontin, a chemical complex between casein phosphoprotein and nanoclusters of amorphous calcium phosphate, nature identical substitutes thereof, and mixtures thereof. In a particular embodiment of the invention the compound sold under the tradename phoscal, which is a chemical complex between casein phosphoprotein and nanoclusters of amorphous calcium phosphate, is selected as the re-mineralization agent.

In another embodiment the re-mineralization agents are selected from the group consisting of calcium, fluoride, osteopontin, and a chemical complex between casein phosphoprotein and nanoclusters of amorphous calcium phosphate (tradename phoscal).

In the most preferred embodiment the re-mineralization agents are selected from the group consisting of sodium fluoride, dicalcium phosphate, and carbamide.

As chewing gum stimulates saliva, and a wide range of active ingredients can be added to the chewing gum according to the invention that promotes re-mineralization or alternatively inhibits demineralization, the re-mineralization effect of the chewing gum exceeds the effect of brushing of teeth.

Calculus may be defined as hardened deposit composed of mineralised plaque and saliva. Hence, by the term "anti-calculus agents" as used herein is meant any agent, which is able to prevent or reduce the formation of hardened deposit composed of mineralised plaque and saliva.

Anti-calculus agents suitable for use in the chewing gum according to the invention include phosphates, pyrophosphates, alkali-metal pyrophosphates, polyphosphates, phosphonates, polyphosphonates and mixtures of any of these. Pyrophosphates are among the best known for use in dental care products. The pyrophosphate salts useful in the present invention include the di-alkali metal pyrophosphate salts, tetraalkali metal pyrophosphate salts and mixtures of any of these in their unhydrated as well as hydrated forms are the preferred species. Disodium di-hydrogen pyrophosphate ($Na_2H_2P_2O_7$), tetra-sodium pyrophosphate ($N_4P_2O_7$), and tetrapotassium pyrophosphate ($K_4P_2O_7$) and mixtures thereof are specific examples.

Additional suitable anti-calculus agents include polyacrylates and other polycarboxylates, such as those disclosed in U.S. Pat. No. 3,429,963, U.S. Pat. No. 4,304,766, and U.S. Pat. No. 4,661,341, polyepoxysuccinates, such as those disclosed in U.S. Pat. No. 4,846,650, ethylenediaminetetraacetic acid as disclosed in British Patent No. 490,384, nitrilotriacetic acid and related compounds as disclosed in U.S. Pat. No. 3,678,154, polyphosphonates as disclosed in U.S. Pat. Nos. 3,737,533, 3,988,443, and 4,877,603.

Suitable anti-calculus agents can e.g. be selected from vitamin C, citric acid, and acetic acid.

Preferably the anti-plaque agents are agents that can be selected from zinc acetate, ammonium carbamate, eucalyptus, cranberry, xylitol, chlorhexidine, seaweed, osteopontin and/or baking soda.

Preferably the anti-gingivitis agents are agents that can be selected from chlorhexidine, myrrh, neem, sage, aloe vera, hexatidine, osteopontin, quince, and/or IG-LY 4023 (Tradename, immuglobuline-lysozyme powder obtainable from Pedersen's Laboratorium, Vejle, Denmark).

Preferably the anti-calculus agents are agent that can be selected from vitamin C, citric acid, and acetic acid.

Preferably the re-mineralisation agents are agents that can be selected from calcium, fluoride, osteopontin, and/or phoscal (tradename for a chemical complex between casein phosphoprotein and nanoclusters of amorphous calcium phosphate).

Preferably the whitening agents can be selected from baking soda, Icelandic moss, bamboo, calcium pyrophosphate, calcium carbonate, sodium hexa-metaphosphate and/or sodium hexa-metaphosphate.

Preferably the fresh-breath agents can be selected from zinc acetate, coriander, green tea, propolis, tea tree oil, barberry bark, hexetidine, champes, sunphenol, applephenol, red tea, green tea extract, white tea and/or thyme extract.

In the following the whitening agents may also be referred to as active cosmetic ingredients. Similar, the fresh-breath agents may be referred to as active cosmetic ingredients, Moreover in the following the anti-plaque agents, the anti-gingivitis agents, the re-mineralization agents, and the anti-calculus agents may be referred to as active therapeutic ingredients.

Although the latter agents may be referred to as active therapeutic ingredients, it is to be understood that in the context of the present invention the agents are used for a non-therapeutic application as a toothbrush substitute.

In a preferred embodiment of the compressed chewing gum tablet according to the invention the chewing gum tablet further comprises one or more taste ingredients selected from sweeteners, high-potent sweeteners and flavours. The addition of taste ingredients acts to make the user chew on the gum for longer time, because it is pleasant to do so. The taste ingredients do in this manner increase the effects of the agents.

When taste ingredients like sweeteners and flavours are used, these are normally admixed to the gum base or gum granules before the active ingredients.

The compressed chewing gum tablet according to the invention is preferably a chewing gum wherein up to 55% of the active therapeutic ingredients are released after 5 minutes of chewing when measured according to Ph. Eur. Version 5.0, 01/2005, paragraph 2.9.25 (volume 1 page 260) (European Pharmacopoeia 5.0). Preferably at least 75% of the active therapeutic ingredients are released after 15 minutes of chewing when measured according to Ph. Eur. Version 5.0, 01/2005, paragraph 2.9.25 (volume 1 page 260). In this manner it is secured that sufficient amounts of the active therapeutic ingredients are released within the preferred chewing time of 5 to 20 minutes.

Moreover, the chewing gum according to the invention is preferably a chewing gum wherein at least 30% of the active cosmetic ingredients are released after 5 minutes of chewing when measured according to Ph. Eur. Version 5.0, 01/2005, paragraph 2.9.25 (volume 1 page 260). Preferably at least 50% of the active cosmetic ingredients are released after 10 minutes of chewing when measured according to Ph. Eur. Version 5.0, 01/2005, paragraph 2.9.25 (volume 1 page 260). This preferred embodiment of the invention provides for sufficient amounts of the active cosmetic ingredients are released within the preferred chewing time of 5 to 20 minutes.

The compressed chewing gum tablets are manufactured from compressed granules. Thus, the gum base is present as granules and is mixed with the active agents, which may also be present as granules or powder and optionally other ingredients. The mixture is filled into a press that presses the mixture to form compressed chewing gum tablets. Use of granules is particular advantageously when one or more of the active ingredients are sensitive towards elevated temperatures as the mixing and pressing can be done at low temperature, e.g. normal room temperature.

The granules used according to the invention may be constituted by gum base (pure gum base) or may be constituted by gum base mixed with one or more agents and optionally sweeteners and flavours. The granules comprising gum base may also be referred to as gum granules. The gum granules may have a size corresponding to an average diameter in the range of 0.0001-2 mm, preferably in the range of 0.001-1.8 mm, more preferred in the range 0.5-1.5 mm. (average diameter of the gum granule corresponds to the diameter of a sphere having the same volume as the gum granule). Consequently, in one embodiment the gum granules are gum powders. In another embodiment the gum granules are or gum base powders.

The gum granules may be manufactured by underwater pelletising or by freezing a gum material and breaking it into granules or powder. Both techniques are familiar to the skilled person.

Compressed chewing gum may in some embodiments preferably be mixed with flavours and/or sweeteners.

Moreover, the chewing gum according to the invention may be centre filled compressed chewing gum tablets (centre filled with liquid, gel or powder), or coated compressed chewing gum tablets. Preferably the compressed chewing gum tablet has an average weight of about 0.5 to 5 g, preferably from 1.5 to 3.5 g.

According to the invention it is preferred that the one or more anti-plaque agents constitute(s) from 0.01 to 70% of the chewing gum (the high level of up to 70% of anti-plaque agents is relevant with respect to xylitol, which may be added in very high amounts to act as an anti-plaque agent). Preferably the anti-plaque agents constitute 0.03-50%, more preferred 0.05 to 35% of the chewing gum.

Preferably the one or more anti-gingivitis agents constitute(s) 0.01-20%, more preferred 0.03 to 12% of the chewing gum.

Preferably the one or more anti-calculus agents constitute 0.01-20%, more preferred 0.03-15% of the chewing gum.

Preferably the one or more re-mineralization agents constitute 0.01-20%, more preferred 0.02-10% of the chewing gum.

Preferably the one or more whitening agents constitute 0.01-20%, more preferred 0.03-12% of the chewing gum.

Preferably the one or more fresh-breath agents constitute 0.01-20%, more preferred 0.02-8% of the chewing gum.

The above listed ranges for content of active ingredients has proven to provide an effective amount of active therapeutic and cosmetic ingredients. Preferably, the total amount of active ingredients does not exceed 35% (with the exception of xylitol, which may be used in higher amounts as described above) based on the total weight of the chewing gum. Preferably, the active therapeutic ingredients constitutes from about 5 to 25%, and the active cosmetic ingredients constitutes from about 0.5 to 15% of the chewing gum based on the total weight of the chewing gum.

In a preferred embodiment of the compressed chewing gum tablet according to the invention the gum base further includes at least one antibacterial agent, preferably selected from xylitol, chlorhexidine, neem, green tea, thyme, and Icelandic moss, and the antibacterial agent preferably constitutes about 0.4 to 7.5% of the chewing gum.

The present invention also relates to use of gum base including at least three active therapeutic ingredients selected from anti-plaque agents, anti-gingivitis agents, anti-calculus agents, and remineralization agents, at least one active cosmetic ingredients selected from whitening agents and at least one cosmetic agent selected from fresh-breath agents for the manufacture of a chewing gum for daily tooth cleaning. The realization that a chewing gum for daily tooth cleaning can be manufactured is in fact very surprising, as the common teaching clearly states that a toothbrush and toothpaste is required for daily tooth cleaning.

By using gum base including at least three active ingredients with therapeutic effect, at least one active cosmetic ingredient with whitening effect and at least one active cosmetic ingredient with fresh-breath effect, a chewing gum having excellent properties in respect of avoiding gingival damage and, furthermore, having sufficient cleaning effect to be capable to ensure an effective daily cleaning of teeth is obtained.

According to the invention the manufactured chewing gum is intended for chewing pieces thereof one, two or more times per day and preferably the chewing gum is intended for chewing one piece thereof in about 5 to 20 minutes. When chewing pieces of chewing gum according to the invention for about 5 to 20 minutes at least once a day a very efficient cleaning of the teeth and the mouth is obtained, including a very satisfactory feeling of cleanness and fresh breath for the user.

Preferably the anti-plaque agent comprises at least one agent that can be selected from zinc acetate, ammonium carbamate, eucalyptus, cranberry, xylitol, chlorhexidine, seaweed, osteopontin and/or baking soda.

Preferably the anti gingivitis agent comprises at least on agent that can be selected from chlorhexidine, myrrh, neem, sage, aloe vera, hexatidine, osteopontin, quince, and/or IG-LY 4023 (tradename for immuglobuline-lysozyme powder, obtainable from Pedersen's Laboratorium, Vejle, Denmark).

Preferably the anti-calculus agent comprises at least one agent that can be selected from vitamin C, citric acid, and acetic acid.

Preferably the re-mineralization agent comprises at least one agent that can be selected from calcium, fluoride, osteopontin, and/or Phoscal (tradename for chemical complex between casein phosphoprotein and nanoclusters of amorphous calcium phosphate).

Preferably the whitening agent comprises at least one agent that can be selected from baking soda, Icelandic moss, bamboo, calcium pyrophosphate, calcium carbonate, sodium hexa-metaphosphate and/or sodium hexa-metaphosphate.

Preferably the fresh-breath agent comprises at least one agent that can be selected from zinc acetate, coriander, green tea, propolis, tea tree oil, barberry bark, hexetidine, champes, sunphenol, applephenol, red tea, green tea extract, white tea and/or thyme extract.

In a further preferred embodiment the gum base includes at least one antibacterial agent, preferably selected from xylitol, chlorhexidine, neem, green tea, thyme, and Icelandic moss.

To counteract caries the gum base, in one embodiment, further includes at least one anti-caries agent, preferably selected from fluoride, phoscal, and apple polyphenol.

In order to ensure a satisfactory taste it is preferred that the gum base further include at least one taste ingredient, preferably selected from sweeteners, high-potent sweeteners, and flavours. The taste ingredients correspond to those previously described.

In some preferred embodiments the manufactured compressed chewing gum tablet is layered providing the previously described advantages.

Furthermore, in various preferred embodiments the manufactured compressed chewing gum tablet is coated and providing the previously described advantages.

The present invention also relates to a method for avoiding abrasive damage on teeth, wherein daily tooth brushing is replaced by chewing of chewing gum. The method provides an unexpected opportunity to avoid abrasive damage on teeth caused by the use of toothbrush and toothpaste. With this method the use of toothbrush and toothpaste become superfluous. The method has the further advantages that the cleaning of teeth by chewing chewing gum can be performed any where at any time.

According to the method pieces of the chewing gum is chewed one, two or more times per day and preferably a piece of the chewing gum is chewed for about 1 to 5 minutes. It has appeared that chewing within the afore-mentioned ranges provide for the best results for tooth cleaning.

Furthermore, the chewing gum is a chewing gum of the above-described type.

The invention will now be further illustrated with reference to some examples.

Gum base refers in general to any commercially available gum base suitable for production of chewing gum. Such gum bases are well-known and available on the market and normally comprise natural and/or synthetic resins and optionally other ingredients. The gum base may be biodegradable.

Chewing gum is the final product, including gum base, active ingredients and optional other ingredients such as taste ingredients and colouring agents. The chewing gum is ready to use by the consumer for cleaning teeth.

Active therapeutic ingredient means any ingredient that has an active therapeutic effect on the teeth and the oral environment including gingiva. Some active therapeutic ingredients may be active against more than one condition, e.g. function as both anti-plaque agent and anti-calculus agent and is this contest listed under both functions. The active agents (e.g. agents active in relation to a specific condition as explained above) are normally present in an amount sufficient to affect the specific condition. If required or desired the amount of an agent present in the compressed chewing gum tablet according to the invention can be increased or decreased in order to obtain a level of the tooth cleaning effect that can be compared with the tooth cleaning effect of a toothbrush.

Anti-plaque agents are any agents that have a specific therapeutic effect of preventing or inhibiting the formation of plaque or degrading or removing existing plaque formations.

Anti-gingivitis agents are any agent that has a specific therapeutic effect of preventing or inhibiting gingivitis or of minimizing or removing existing gingivitis.

Anti-calculus agents are any agents that has a specific therapeutic effect of preventing or inhibiting calculus.

Re-mineralization agents are any agent that has a specific therapeutic effect in improving the degree of re-mineralization of the teeth or avoiding de-mineralization of the teeth.

Active cosmetic ingredients are ingredients that have an active cosmetic effect on the teeth and oral cavity, i.e. improving the appearance of the teeth including odour.

Whitening agents are any agents that are capable of bleach or whiten teeth.

Fresh-breath agents are any agents that provide a fresh and pleasant-smelling breath.

All percentages (%) are weight percentages unless otherwise stated.

The chewing gum according to the invention can be conventional chewing gum pieces, compressed chewing gum tablets, sticks, centre-filled chewing gum with the centre filled with liquid, gel or powder. Moreover, the active ingredients, flavour and sweetener may be encapsulated to avoid undesired reactions during storage.

BRIEF DESCRIPTION OF DRAWING

FIG. 1 illustrates an estimate of the efficacy of the chewing gums tested (C.G) (chewing for 5 to 20 minutes) for dental care purposes compared with tooth brushing (T.B) (new toothbrush and correct tooth brushing for 2 minutes).

The line at 1 indicates the efficacy of a toothbrush and the columns indicates the efficacy of chewing gum in respect of plaque, whitening, fresh breath, gingivitis, calculus, re-mineralization and abrasive damage, respectively. As indicated by the line, the overall efficacy of tested chewing gum compared to tooth brushing is about 67%. The individual effects can be improved by adding more active ingredients and/or by combining ingredients so that the efficacy is raised above 70%, such as an efficacy that exceeds 100% or better efficacy than tooth brushing.

In respect of plaque (efficacy approx 60% for the tested chewing gum) the removal of plaque and/or inhibition of plaque formation can been improved, e.g. by adding zinc acetate to the chewing gum, which will enhance the effect to be close to or better than the efficacy for brushing teeth. In addition, the chewing gum according to the invention will be better than brushing teeth in real life due to the fact that the effect from chewing gum reaches places the toothbrush cannot reach. An in vivo plaque study performed by the inventors shows that e.g. zinc acetate worked in the "hard-to-reach" places with high efficiency.

Moreover, a clinical test has demonstrated that chewing gum with calcium pyrophosphate clinically whitens teeth. Presently, the effect almost matches the effect of a toothbrush with toothpaste. However, by using other agents the whitening effect will reach 100% as compared with tooth brushing.

The fresh breath effect is already better than if brushing teeth, as the chewing gum according to the invention has a much longer contact time with the volatile sulphur compounds to be eliminated. Correct tooth brushing last 2 minutes whereas chewing of chewing gum last for at least 5 minutes.

With respect of the anti-gingivitis effect, chewing gum according to the invention already match this effect compared to brushing of teeth, as the contact time is longer as with brushing teeth, thereby allowing the active substances longer time to affect the infected gingiva.

As chewing gum stimulates saliva, and a wide range of active ingredients can be added to the chewing gum according to the invention that promotes re-mineralization or alternatively inhibits demineralization, the re-mineralization effect of the chewing gum exceeds the effect of brushing of teeth.

The chewing gum according to the present invention substantially has no damaging effect on softer portions of the teeth or on the gingival tissue, and this parameter is naturally dramatically better than brushing teeth.

Example 1

The chewing gum in the following example was manufactured from a commercially available gum base (Danfree, available from Gumlink A/S, Vejle, Denmark) mixed with sweeteners, taste ingredients and active ingredients. The chewing gum was manufactured as a two-layer product and the gum material for the two layers was produced with the following ratios:

Formulation 1:

| | |
|---|---|
| Gum base | 60.00% |
| Sorbitol | 18.20% |
| Peppermint powder | 1.50% |
| Menthol powder | 0.30% |
| Dicalciumphosphate | 2.70% |
| Green tea | 5.00% |
| Baking soda | 0.40% |
| Calcium carbonate | 4.10% |
| Calcium pyrophosphate | 6.50% |
| Succralose | 0.25% |
| Magnesium stearate | 0.50% |
| *Eucalyptus* powder | 0.50% |

Formulation 2:

| | |
|---|---|
| Gum base | 30.00% |
| Xylitol | 68.80% |
| Peppermint powder | 0.50% |
| Menthole powder | 0.20% |
| Magnesium stearate | 0.50% |

The gum base was granulated (GALA underwater pelletizer) to form granules with diameters in the range of approximately 0.5-1.5 mm and mixed with the active ingredients.

The particulate mixture of formulation 1 (1.5 g) was filled into a tabletting machine and compressed to form a first layer. Then 0.7 g pure gum base granules were filled into the tabletting machine and compressed onto the first layer to form a barrier layer. Finally 2 g of formulation 2 particulate material was filed into the tabletting machine and compressed.

The resulting cylindrical shaped layered chewing gum tablets had an average weight of about 4.2 g and a diameter of about 8 mm.

The chewing gum was evaluated for inhibition of plaque formation in a clinical study.

The test subjects abstained from all oral hygiene for 2 days and either chewed the gum five times per day or used no gum (Plaque scores were assigned using the Modified Quickly-Hein (MQH) index). The result demonstrated that chewing gum comprising xylitol was significantly more effective in inhibiting the formation of plaque on teeth when used as the only means of oral hygiene for two days. Additionally, it was most efficient in areas that are often missed during tooth brushing.

In conclusion, the results demonstrate that the chewing gum containing xylitol is able to reduce dental plaque formation. Moreover, the chewing gum has an ability to make dental plaque less adhesive and thus easier to remove during chewing. As a further benefit, xylitol inhibit bacterial growth and thereby inhibit tooth decay.

The chewing gum was also evaluated for its whitening effect. The chewing gum comprising calcium pyrophosphate not only results in whiter teeth by stain removal, it also helps to prevent further stain after consumption of foods and beverages.

Clinical studies on the inhibition of stain over a 14 days period showed that when chewing, chewing gum according to the invention 20 minutes each day, compared to chewing, chewing gum with 4.5% calcium carbonate, commercially available on the market, the inhibition of stain was considerably improved.

The dicalcium phosphate in the chewing gum improves the remineralization rate of the teeth.

Green tea provided excellent fresh breath properties in the chewing gum.

Further studies of the effects of the chewing gum according the invention were performed as described below. For the purpose of the studies two types of chewing gum were prepared as compressed chewing gum tablets. The active agents (not present in the placebo) were mixed into the gum base to form a mixture and the mixture was formed into gum granules. The gum granules were mixed with sweeteners and flavours and filled into a tabletting machine producing compressed tablets. The formulations of the chewing gum tablets used in Examples 2 to 5 are shown in Table 1 below.

TABLE 1

| Ingredient | A: According to the invention | B: Placebo | C: According to the invention |
|---|---|---|---|
| CRP base | 20.00 | 20.00 | 20.00 |
| Base | 20.00 | 20.00 | 20.00 |
| Sorbitol | 30.39 | 52.10 | 31.01 |
| Maltitolsyrup | 5.00 | 5.00 | 5.00 |
| Lecithine | 0.2. | 0.20 | 0.20 |
| Green tea extract | 1.25 | | 1.25 |
| Phenol | 0.52 | | 0.52 |
| Aronia | 1.25 | | 1.25 |
| Osteopontin | 0.02 | | |
| Zinc acetate | 0.06 | | 0.06 |
| Fluoride | 0.03 | | 0.03 |
| NaHCO$_3$ | 1.04 | | 1.04 |
| Calcium carbonate | 3.00 | | 3.00 |
| Dicalicium phosphate | 2.30 | | 2.30 |
| Calcium pyrophosphate | 6.80 | | 6.80 |
| titandioxid | 1.00 | | 1.00 |
| Thyme | 0.24 | | 0.24 |
| Acesulfame | 0.20 | 0.20 | 0.20 |
| Aspartame | 0.20 | 0.20 | 0.20 |
| Peppermint | 1.00 | 1.00 | 1.00 |
| *Eucalyptus* | 1.00 | 1.00 | 1.00 |
| Menthol | 0.30 | 0.30 | 0.30 |
| Xylitol | 4.20 | | 4.20 |
| Sum | 100.00 | 100.00 | 100.00 |

Four different studies were performed:
A study for assessing oral malodor
A study for assessing re-mineralisation
A study for assessing whitening
A study for inhibiting dental plaque The four studies were performed and supervised by a qualified dentist in order to assess the effect of the chewing gum according to the invention.

Example 2

Study for Assessing Oral Malodor

The purpose of this study was to demonstrate the efficacy of chewing gum containing green tea extract and zinc in reducing oral malodor (OM) as compared to a placebo.

Methods & Materials:

The investigation was a longitudinal study, which determined efficacy of the chewing gum in reducing oral malodor. A total of 20 subjects with self proclaimed oral malodor (OM) that has been verified by an organoleptic judge (OJ) were selected for this randomized clinical trial. Subjects were instructed to chew the provided gum five times a day for 20 minutes each time for a period of seven days.

Qualified subjects completed a demographic and a medical history survey and were assessed for degrees of OM. The qualifying score of the subjects as determined by self-proclamation and OJs was minimum of 2 or above on the 5-point malodor scale. Baseline (day 0) and post treatment (day 7) examinations included: 1) organoleptic tests 2) oral soft tissue evaluation 3) OralChroma. The results of baseline and post treatment examinations for organoleptic scores were scored on the 5-point malodor scale as described below. 20 subjects were randomly assigned to the one of the following groups with 10 subjects to each group:

Group 1: Subjects using chewing gum containing the active ingredient (formulation A, table 1),
Group 2: Subjects using placebo chewing gum (formulation B, table 1).

All groups were instructed in routine oral hygiene procedures. Subjects in Groups 1 and 2 were instructed on the use of the chewing gum. Test articles were then distributed to subjects of each group. The groups were requested to perform the assigned procedures at home for a period of seven days. Subjects were asked to keep a daily diary during the seven-day period to record compliance to the instructions and procedures given. At the end of the seven-day period, the clinical post treatment examinations previously mentioned were repeated on each subject. The data collected at the baseline examination and at the post treatment examination were then compared and statistically analyzed.

20 adult male/female subjects were enrolled to complete the evaluation as required. Subjects were eligible to enter the study if they met the following selection criteria: over the age of 18 years and in good general health, willingness to sign the informed consent form and comply with protocol procedures, a minimum OM score of 2 on the 5-point malodor scale, a minimum of 16 natural teeth including at least 4 molars, and availability to complete the seven-day study. They were excluded if they had gross oral pathoses, orthodontic devices, partial or complete dentures, any systemic disease, periodontal disease, or gross oral hygiene neglect, were pregnant or lactating women, were chronic smokers, or were on prophylactic antibiotic coverage for routine dental therapy and used systemic antibiotics for a period of more that seven days prior to the study, or were participating in other dental or investigational trials.

An IRB approved informed consent statement was reviewed and signed by each subject. After final eligibility was ascertained by the inclusion/exclusion criteria, a distinct subject number was assigned to each subject.

Diagnostic Tests:
Organoleptic Assessment:

Two OJs trained and calibrated according to the protocol developed by UHRG & University of Minnesota made two separate assessments on each subject. Each subject was instructed to close their mouths without swallowing for a period of two minutes. After two minutes the subject breathed out gently, at a distance of 10 cm from the nose of the OJ. The odors were assessed according to the 5-point scale: 1=No perceived odor, 2=Faint odor, 3=Moderate odor, 4=Strong odor, 5=Extremely strong odor.

Clinical Examinations
Oral Soft Tissue Assessment:

The oral cavity was assessed for irregular tissue, canker sores, or cancer lesions. Subjects with gross periodontal disease, calculus, bridges, or dentures were excluded from the study.

OralChroma:

OralChroma is a gas chromatographer and typically consistent measurements may vary due to differences in human breath gases. Subjects were instructed to avoid eating, drinking, brushing, flossing or scraping their tongue for at least 2 hours prior to providing breath samples. The subject held the syringe in his/her sealed oral cavity for 30 seconds without touching the tip of the syringe with his/her tongue. After the 30-second period the syringe was filled with a breath sample. The syringe was wiped after removal from the subject's mouth to remove any saliva and the needle was placed onto the syringe for injection into the machine.

The time between the removal of the syringe from the subject's mouth and injecting the sample into the Oral-Chroma was minimized to avoid any changes in the concentration of the breath gases as the temperature of the sample decreases from the body temperature to room temperature. Only ½ ml of the breath sample was injected into the Oral-Chroma. A new syringe was used for each subject to avoid contamination.

All subjects completed a daily account of their assigned procedures in order to record compliance with the requirements of the protocol as well as any complaints or comments.

Test Products:

The chewing gum test products were supplied for each subject by Gumlink A/S, Denmark, in coded containers as defined in the study protocol. The test products were assigned after each subject was enrolled and assigned a subject number.

Results:

Subjects in Group 1 who used the chewing gum containing the active ingredient positively reported that they enjoyed the great taste and freshness of the mouth that the gum provided, and released a good blast of taste in the beginning. They also reported that the tasty gum was long lasting and worked for reducing OM. Subjects in Group 1 negatively reported that the gum tasted medicinal and had a bad after-taste after the first initial minutes of chewing. Subjects also reported that the taste went away quickly, and after chewing for 20 minutes it felt like chewing cardboard and left the mouth and tongue dry. Other subjects reported that there was excessive saliva produced from chewing, or that the gum started to break apart into loose sand-like particles.

Subjects in Group 2 who used the placebo positively reported that the gum had a great taste with a good flavor and made the mouth and tongue feel clean, leaving fresh breath even after chewing. Subjects also reported that they felt the gum worked to reduce OM and helped to get rid of food particles in the mouth. Subjects in Group 2 negatively reported that they did not like the flavor of the gum; some reported that the flavor was not strong enough and faded too fast, others reported that the flavor was too strong. Subjects also reported that chewing the gum in the morning did not appear to help reduce OM due to the bad taste on the tongue, it was too difficult to chew two pieces of gum at the same time, and that the gum became stiff while chewing.

Statistical Analysis was performed to compare various OM parameters. Absolute mean changes and percentage mean changes for all the OM parameters over time and between each group was performed and p-values were calculated. 20 subjects were enrolled in the study, nine subjects in Group 1 completed the study, and eight subjects in Group 2 completed the study.

Eight variables were measured in each subject, once on day 0 and once on day 7. The means and standard error for each group and the mean difference, the standard error of the mean difference and the corresponding p-values for comparison for the groups were calculated. The p values that are statistically significant are ($p<0.10$).

The analysis of covariance in a repeated measures model was used. The chewing gum A containing the active product was found to be significantly more effective overall in reducing morning breath.

The results are shown in Table 2 and Table 3 below.

TABLE 2

Summary of Baseline and Day 7 Oral Malodor Assessment Scores for Subjects Who Completed the 1 Week Study

| Parameter | Treatment | Summary | Baseline Difference Mean ± SD | Significance | Summary | Day 7 Difference mean +/− SD | Significance |
|---|---|---|---|---|---|---|---|
| Organoleptic 1 | Active | 3.82 ± 0.32 | Placebo 0.32 ± 0.47 | P = 0.5032 | 1.00 ± 0.28 | Placebo −1.88 ± 0.42 | P < 0.0001 |
|  | Placebo | 3.50 ± 0.34 |  |  |  |  |  |
| Organoleptic 2 | Active | 3.91 ± 0.32 | Placebo 0.51 ± 0.46 | P = 0.2742 | 1.10 ± 0.29 | Placebo −1.78 ± 0.43 | P = 0.0002 |
|  | Placebo | 3.40 ± 0.32 |  |  |  |  |  |
| Oral Chroma $H_2S$ (ng/10 ml) | Active | 3.03 ± 0.41 | Placebo 0.02 ± 0.60 | P = 0.9772 | 0.77 ± 0.28 | Placebo −2.33 ± 0.43 | P < 0.0001 |
|  | Placebo | 3.01 ± 0.44 |  |  |  |  |  |
| Oral Chroma $CH_3SH$ (ng/10 ml) | Active | 2.38 ± 0.58 | Placebo −1.46 ± 0.84 | P = 0.0907 | 0.57 ± 0.46 | Placebo −3.65 ± 0.69 | P < 0.001 |
|  | Placebo | 3.85 ± 0.61 |  |  |  |  |  |
| Oral Chroma $(CH_3)_2S$ (ng/10 ml) | Active | 1.40 ± 0.23 | Placebo 0.38 ± 0.34 | P = 0.2709 | 0.42 ± 0.18 | Placebo −0.60 ± 0.26 | P = 0.0305 |
|  | Placebo | 1.02 ± 0.24 |  |  |  |  |  |
| Oral Chroma $H_2S$ (ppb) | Active | 300.73 ± 32.34 | Placebo 145.53 ± 46.86 | P = 0.0037 | 74.20 ± 26.23 | Placebo −96.68 ± 39.35 | P = 0.0194 |
|  | Placebo | 155.20 ± 33.91 |  |  |  |  |  |
| Oral Chroma $CH_3SH$ (ppb) | Active | 133.18 ± 23.75 | Placebo 54.78 ± 34.41 | P = 0.1018 | 45.80 ± 17.69 | Placebo −29.08 ± 26.54 | P = 0.2811 |
|  | Placebo | 75.40 ± 24.90 |  |  |  |  |  |
| Oral Chroma $(CH_3)_2SH$ (ppb) | Active | 10.27 ± 5.56 | Placebo −3.83 ± 8.06 | P = 0.6378 | 2.90 ± 4.57 | Placebo −9.35 ± 6.86 | P = 0.1821 |
|  | Placebo | 14.10 ± 5.83 |  |  |  |  |  |

TABLE 2-continued

Summary of Baseline and Day 7 Oral Malodor Assessment Scores for Subjects Who Completed the 1 Week Study

| Parameter | Treatment | Summary | Baseline Difference Mean ± SD | Significance | Summary | Day 7 Difference mean +/− SD | Significance |
|---|---|---|---|---|---|---|---|

Table 2. Summary of eight OM parameters at baseline (day 0) and day 7. Organoleptic 1 and Organoleptic 2 represent the mean OM assessment scores of OJ1 and OJ2, respectively. The chewing gum containing the active ingredient was statistically significant ($p < 0.001$) in reducing oral malodour compared to the placebo group for both the scores from Organoleptic 1 and Organoleptic 2. The OralChroma measures hydrogen sulphide ($H_2S$), methyl mercaptan ($CH_3SH$), and dimethyl sulphide (($CH_3)_2SH$) in ng/10 ml and parts per billion (ppb). The chewing gum containing the active ingredient was statistically significant ($p < 0.001$) for reducing hydrogen sulphide compared to the placebo. Methyl mercaptan was also statistically significantly ($p < 0.001$) reduced compared to the placebo.

TABLE 3

Summary of the Difference in Oral Malodor Scores After 7 days of treatment

| Parameter | Treatment | Summary | Difference mean +/− SD | Significance |
|---|---|---|---|---|
| Organoleptic 1 | Active | −2.80 ± 0.22 | Placebo −2.05 ± 0.33 | P < 0001 |
|  | Placebo | −0.75 ± 0.25 |  |  |
|  | Control | 0.00 ± 0.22 |  |  |
| Organoleptic 2 | Active | −2.08 ± 0.22 | Placebo −2.18 ± 0.33 | P < 0.0001 |
|  | Placebo | −0.63 ± 0.25 |  |  |
|  | Control | −0.10 ± 0.22 |  |  |
| Oral Chroma $H_2S$ (ng/10 ml) | Active | −2.35 ± 0.36 | Placebo −2.18 ± 0.54 | P = 0.0003 |
|  | Placebo | −2.9A6 ± 0.38 |  |  |
|  | Control | −0.20 ± 0.36 |  |  |
| Oral Chroma $CH_3SH$ (ng/10 ml) | Active | −1.,84 ± 0.39 | Placebo −1.93 ± 0.59 | P = 0.0038 |
|  | Placebo | −0.01 ± 0.44 |  |  |
|  | Control | −0.18 ± 0.39 |  |  |
| Oral Chroma $(CH_3)_2S$ (ng/10 ml) | Active | −1.03 ± 0.12 | Placebo −0.95 ± 0.18 | P = <0.0001 |
|  | Placebo | −0.18 ± 0.12 |  |  |
|  | Control | −0.18 ± 0.12 |  |  |
| Oral Chroma $H_2S$ (ppb) | Active | −222 ± 21.91 | Placebo −208.75 ± 32.86 | P = <0.0001 |
|  | Placebo | −13.25 ± 24.49 |  |  |
|  | Control | −38.9 ± 21.91 |  |  |
| Oral Chroma $CH_3SH$ (ppb) | Active | −77.60 ± 13.56 | Placebo −62.48 ± 20.34 | P = 0.0042 |
|  | Placebo | −15.13 ± 15.16 |  |  |
|  | Control | −6.90 ± 13.56 |  |  |
| Oral Chroma $(CH_3)_2SH$ (ppb) | Active | −7.50 ± 3.29 | Placebo −6.25 ± 4.93 | P = 0.2137 |
|  | Placebo | −1.25 ± 3.67 |  |  |
|  | Control | −0.30 ± 3.29 |  |  |

Table 3. Summary of differences in OM scores between baseline (day 0) and day 7. The chewing gum containing the active ingredient was statistically significant ($p < 0.001$) in reducing OM compared to the placebo for Organolaeptiv 1 and Organoleptic 2. The chewing gum containing the active ingredient was statistically significant ($P < 0.001$) in reducing dimethyl sulphide and hydrogen sulphide in ppb compared to the placebo.

Example 3

Study for Assessing Re-Mineralization

Materials and Methods:
Demineralization Solution Preparation:

The demineralizing buffer solutions was made up of analytical-grade chemicals and deionized water. It contained 2.2 mM $CaCl_2$, 2.2 mM $NaH_2PO_4$, 0.05 M acetic acid and pH was adjusted with 1 M KOH to 4.4.

Artificial Enamel Carious Lesion Formation:

Sound extracted molars were cleaned of any soft tissue debris and inspected for cracks, hypoplasia, and white spot lesions under the stereomicroscope. The teeth were then coated with acid-resistant varnish (Lancester, Germany), leaving a narrow 'window', approximately 1 mm wide, on the sound, intact surface of the buccal and/or lingual enamel. Each tooth was immersed, for 96 hours, in 10 ml of demineralizing solution in order to produce lesions of about 130-180 µm deep. The teeth were sectioned longitudinally through the lesions, approximately 100-150 µm thick, by a hard tissue microtome (Leica 1600, Wetzlar, Germany). Seventy-two sections were randomly selected and equally divided into three groups, i.e. twenty-four sections per group. Every section was studied using PLM (Orthoplan, Leitz, Germany) and MRG (Softex ISR-20, JIRA, Japan), respectively, in order to record the depth and mineral content of the lesion at baseline before the 21-day intra-oral experimental period. The same evaluation techniques were utilized to record the lesion characteristics after the intra-oral period.

Prior to being attached to an intra-oral appliance, each section was painted, under a stereomicroscope, with acid-resistant varnish leaving only the lesion surface exposed to the oral environment. After the intraoral test phase of the experiment, this nail varnish was removed by immersing each enamel section in acetone for 10 s and thoroughly rinsed with deionized water. The sections were stored in a 100% humidity environment until used. This was achieved by suspending the specimens, using dental floss, over deionized water in a beaker which was sealed with paraffin (Para film, USA).

Test Groups:

There were three experimental groups coded as A, B and C, respectively. Eighteen healthy volunteers in the age range of 20-33 years participated in this study. After being given verbal and written explanations of the experimental protocol, informed consent was obtained from all of the volunteers. The oral hygiene status of each individual was checked to confirm that they had good oral hygiene, no active dental caries, no enamel fluorosis, and no gingival/periodontal or mucosal pathology.

Experimental Protocol:

After the protocol has been approved by the Faculty Ethics Committee, upper and lower alginate impressions of the subject's dentition were taken, and plaster casts were constructed. A modified version of the lower appliance used in our previous study (Itthagarun et al., 2005) was custom made for each subject. Two enamel specimens were mounted horizontally parallel to each other in slightly recessed areas of the appliance, positioned just below the lingual aspect of the mandibular second premolars, giving four specimens per subject. The enamel sections were covered by gauze (Dacron®, C.R. Bard, Billerica, Mass.) to encourage the formation and accumulation of plaque on the surface of enamel. A total of 72 specimens were planned for the experiment i.e. 24 sections per group. The enamel specimens were evaluated for the lesion depth and mineral profile at baseline before being placed in the appliances. Each volunteer was then provided with the appliance without specimens before the actual intra-oral test phase of the experiment to resolve any irritation to the soft tissue that was caused by the appliance.

All of the participants were randomly divided in to 3 groups (six participants in each group):

Group A. Each subject was instructed to wear the appliance and chew a fluoride chewing gum (formulation A, table 1) for 20 minutes immediately after breakfast, lunch, dinner and after snacks (midmorning and mid-afternoon) for a period of 21 days. They were also instructed to clean their teeth using a soft toothbrush once daily (morning) without toothpaste.

Group B. Each subject was instructed to wear the appliance and brush his/her teeth using a soft tooth brush twice daily (morning and night) for up to one minute with a pea sized amount of fluoridated toothpaste (FluoCalcin, 1000 ppmF).

Group C. Each subject was instructed to wear the appliance and brush his/her teeth with a soft tooth brush once daily (morning) for up to one minute without using toothpaste.

The diet of the volunteers was not altered instead it was standardized for all the subjects by recording their food intake for the first week and then giving back a copy of the record with a request that they maintain a similar diet throughout the experimental period. The subjects were also supplied with snack food in accordance with the plaque pH study by Jensen (1986) and instructed to consume two of the provided snacks each day; one mid-morning and one mid-afternoon so as to simulate between-meal snacks.

Subjects wore the intra-oral appliance all the time, for a period of 21 days, including eating and during sleep; it was only removed for tooth brushing. After 21 days, all of the appliances were returned to the operator, except for one from a volunteer in Group A, the enamel specimens were removed from the appliances and re-evaluated for their lesion depth, mineral profile and compared with the baseline data recorded before the intra-oral period.

Two subjects withdrew during the experiment, one from Group A and one from Group B. II. One subject from Group A had not returned the appliance by the time the results were analysed. III. Some of the specimens were broken during the experimental procedures. IV. The total numbers of the specimens at the time of data analysis were therefore 15, 18 and 18 for Groups A, B and C, respectively.

Evaluation Techniques

Qualitative Evaluation:

After imbibition of the sections in water, PLM was employed to evaluate qualitatively the body of the lesion in each of the enamel sections. The sections were expected to show a clear demarcation between sound enamel and an initial lesion. Any changes in the lesion during the experimental period could be detected from the photomicrographs which were taken at a standard magnification before and after experiment.

Quantitative Evaluation:

Enamel sections were exposed to X-ray irradiation at 10 kV and 3 mA for a period of one minute for each section. Standard Kodak chemicals were used for film development. After being developed, each film was mounted and captured in the IBAS 2000 system (Kontron, Germany), which enables automatic measurement of the lesion area and lesion depth both 'before' and 'after' treatment. Thus, an actual change or a percent change was calculated. An image analysis system (Macintosh Quadra 700, USA) was utilized to measure the amount of mineral change before and after treatment within the same lesion these values were used to make comparisons between the three test groups.

Results

The results are shown in Table 4 below.

TABLE 4

Mean values (±SD) of lesion depth, maximum mineral content in the surface zone and the differences in the mineral content of the samples in the three treatment groups.

| Group (n) | Lesion depth (LD) Mean ± SD | Vmax Mean ± SD | Delta Z Mean ± SD |
|---|---|---|---|
| A Before Chewing gum | 174.6 ± 13.0 | 29.6 ± 6.3 | 8605 ± 629.6 |
| After †* (15) % Change | 158.4 ± 17.8 †* 9.1 ± 9.6*** | 33.5 ± 6.8 †* −14.4 ± 18.9 | 7783 ± 902.2 9.3 ± 9.7 *** |
| B Before Fluoride Paste | 161.5 ± 11.7 | 34.3 ± 4.3 | 7919 ± 591.5 |
| After †* (18) % Change | 155.9 ± 11.4 †* 3.4 ± 1.2*** | 36.9 ± 4.5 †* −7.5 ± 5.1 | 7635 ± 570.2 3.5 ± 1.3 *** |
| C Before No-Toothpaste | 169.6 ± 19.4 | 36.8 ± 11.3 | 8319 ± 987.8 |
| After †* (18) % Change | 175.7 ± 14.1 †* −4.1 ± 5.9*** | 32.1 ± 9.8 †* 11.7 ± 13.6 | 8648 ± 715.8 −4.5 ± 6.1 *** |

† paired - t-test
* indicates a significant difference at p < 0.05
*** indicates a significant difference at p < 0.0001 [ANOVA and Student-Newman-Keuls tests]

PLM Observation:

Photomicrographs taken under the PLM (Zeiss, Wetzlar, Germany) which was connected to a computer system (LeicaQuin, Leica, Germany), revealed that the mean and standard deviation (SD) of pre-treatment lesion depth, from each group, ranged from 161±11 μm to 175±14.1 μm. Among these pre-treatment lesion depths, no statistically significant result was obtained (p=0.0523, ANOVA).

The results from the lesion depth measurements after the trial period showed that the lesions were reduced by 9% (174.6±13.1→158.4±17.8), and 3% (161.5±11.7→155.9±11.4) in Groups A and B respectively, while an increase in the lesion depth of about 4% (169.6±19.4→175.7±14.1) was noted in Group C. These values were found to be statistically significant different (p<0.05, pair t-test). ANOVA and Student-Newman-Keuls (SNK) tests also confirmed a statistically significant difference among all treatment groups (p<0.0001).

MRG Observation:

After the 21 day intra-oral test period, the maximum mineral content in the surface zone ($V_m$) of the lesions in Groups A and B increased by 140% and 8% respectively, while the $V_m$ of the group C decreased by 11.7%. A paired -t-test confirmed a statistical significance between the before and after mineral contents in the surface zone of the lesions within each group (p<0.05). However, when comparisons were made among the treatment groups, ANOVA and SNK tests showed no statistically significant difference between Groups A and B (p>0.05), while Groups A and B were statistically significant different from Group C (p<0.0001).

After the 21 intra-oral period, $\Delta Z$ Values showed a decrease of 9% and 4% for Groups A and B, respectively (p<0.05, paired -t-test) while in Group C, the $\Delta Z$ values increased by 4%. A statistically significant difference was noted when comparisons were made among the three treatment groups (p<0.0001, ANOVA, SNK).

SUMMARY

The lesion characteristics recorded (Lesion depth, $V_{max}$, $\Delta Z$) after the intra-oral period, of the lesions in all of the three groups, showed a significant difference from those before the treatment.

After chewing the fluoride containing chewing gums for 21 days, it was found that the mean lesion depth had reduced by 9%, the mineral content in the surface zone of the lesion had increased by 14% while the $\Delta Z$ had decreased by 9%.

After using the fluoride toothpaste, twice a day for 21 days, the mean lesion depth was found to have reduced by 3%, the mineral content in the surface zone of the lesion had increased by 7% while the $\Delta Z$ had decreased by 4%.

After the test period the specimens in the control group showed that their mean lesion depth increased by 4%, the mineral content at the surface zone of the lesion had decreased by 11% while the $\Delta Z$ had increased by 5%.

Although no significant difference was found when the $V_{max}$ data from the Group A (chewing gum) and Group B (fluoride toothpaste) were compared, there was a trend in the results indicating that Group A lesions showed better "healing efficacy" than Group B. However, these values might have reached a level of statistical significant difference if the sample size had been bigger.

Based on the lesion depth and $\Delta Z$ values, it appears that chewing a fluoride containing chewing gum 5 times a day could slow down the progress of demineralization more effectively than brushing twice a daily with a fluoride toothpaste.

Example 4

Study for Assessing Whitening

A special laboratory method has been developed to determine the potential of chewing gums to remove dental stains. The general experimental design consists of using a specially-designed mechanical mastication device to treat stained teeth with chewing gum. (Developed by M.S.D., Ph.D. Carl J. Kleber)

The purpose of this study is to evaluate the whitening effect of chewing gum with different active ingredients (formulation A, table 1) as well as a placebo gum without active ingredients (formulation B), table 1) and compare the results to the whitening effect of brushing teeth with a toothbrush.

The difference in whiteness is measured quantitatively using a colorimeter.

To compare the effect of chewing gum and toothbrush 2 times brushing of 1 minute and 5 times chewing chewing gum of 20 minutes was chosen, in order to simulate a realistic daily use.

Materials & Methods

The chewing gum granules used contains the following raw materials (table 1), where Baking Soda, Calcium Pyrophosphate, Calcium Carbonate and possibly Aronia and Titan, will be effective in the whitening process:

The chewing buffer is a ammoniumdihydrogenphosphat-_solution (1.38 g/L) were pH is adjusted to 7.4 with NaOH.

Specimens was Prepared by Carl Kleber:

Squares of bovine dental enamel were embedded in clear polyester casting resin to provide 1.5 cm square blocks with the labial surface exposed. The specimens were rinsed with deionized water and attached to a staining apparatus in preparation for stain formation.

The tooth staining apparatus was designed to provide alternate immersion into the staining broth and air-drying of the specimens.

The staining broth was prepared by adding 1.02 g of instant coffee, 1.02 g of instant tea, 10 ml of red wine, and 0.75 g of gastric mucin to 250 ml of sterilized trypticase soy broth. Approximately 50 ml of a 24-hour *Micrococcus/uteus* culture was also added to the stain broth. The apparatus, with the enamel specimens attached and the staining broth in the trough was then placed in an incubator at 37° C. with the specimens rotating continuously through the staining broth and air. The staining broth was replaced once every 24 hours. With each broth change, the trough and specimens were rinsed and tooth brushed with deionized water to remove any loose deposits.

Stain Measurement:

The amount of the stain on the teeth was measured by taking colour readings with a Minolta spectrophotometer CM-2600d. Measurements over the entire visible colour spectrum were obtained using the CIELAB colour scale. This scale quantifies colour according to 3 parameters, L* (whiteblack value), a* (red-green chroma), and b* (yellow-blue chroma). In order to obtain reproducible readings, the stained enamel specimens were allowed to air-dry at room temperature for 30 minutes before colour measurements were made. At the end of a test period the stain was removed with sandpaper grain 600, in order to measure how much stain was available to remove.

Measurements were obtained by aligning the center of the 4-mm square segment of stained enamel directly over the 3-mm-diameter targeting aperture of the Minolta@ spectrophotometer. An average of 3 colour readings using the L*a*b* scale were taken for each specimen.

L*100=perfect white

Chewing the Samples:

A mechanical instrument which was developed by Kleber et al. to simulate the human mastication of chewing gum, was used to treat the tooth specimens with the test chewing gum. For testing, a tooth specimen was placed both in the upper and lower tooth holders of the instrument. Then 15 ml of buffer was placed in the reservoir and warmed to 32 degrees C. by a thermostatically-controlled heating element.

When the saliva reached the proper temperature, 2 cores (approximately 2 grams) of chewing gum were inserted between the repositioning paddles directly over the lower tooth specimen. Then the mastication motor was started and the two teeth were treated with the chewing gum for 20 minutes at a rate of 22 chewing cycles/minute. 8 teeth were used with gives 4 repetitions of the chewing. Each tooth was going through 5 cycles of 20 minutes.

Brushing Teeth:

Specimens were fastened and brushed for 1 minute with a normal toothbrush. There was an constant force on the brushing head of 150 g. The teeth was constant moisturised with a toothpaste slurry consisting of ⅓ toothpaste (FluoCalcin Classic) and ⅔ water. The brushing was done by hand and at a frequency of 60 brushing cycles/minute.

8 teeth were used and each tooth was brushed 2 times.

Measurements on the colour change was done before, between and after the 2 chewing periods.

Results

Stain Calculations:

% stain removal at $T_n = (E$ at $T_n/E\text{max difference})*100$

The overall change in the color of the stained teeth was calculated using the CIELAB equation $\Delta E = [(\Delta L^*)^2 + (\Delta a^*)^2 + (\Delta b^*)^2]^{1/2}$. The individual component L* (white) of the L*a*b* scale were also compared separately to determine the specific changes in the whiteness.

Data was tabulated using a spreadsheet program (Excel®, Microsoft), and analyzed by means of conventional statistics.

Statistical significance of data for each category was determined by using a 2-tail T-test $p<0.05$.

TABLE 5

Comparison of the whitening effect between tooth brush 2 * 1 minute and chewing gum 5 * 20 minutes. ΔE represents the overall colour change.
% stain reduction = stain removal/total stain

| Product | ΔE | $\Delta E_{max}$ | % Reduction |
|---|---|---|---|
| TOOTHBRUSH | 3.98 ± 2.09 [a] | 28.43 ± 4.26 [a] | 13.80 [a] |
| PLACEBO GUM B | 1.81 ± 0.51 [b] | 28.39 ± 2.92 [a] | 6.42 [b] |
| GUM A | 4.47 ± 1.51 [a] | 28.41 ± 3.49 [a] | 16.35 [a] |

Two-tailed T-test: Values in the same column with the same letter are not statistically different, those with different letters are different at p < 0.05.

Discussion & Conclusion

The total amount of stained removed from the specimens were significant better in the A chewing gum compared to the placebo gum with no active ingredients. Compared to the toothbrush the A gum also removes more stain, but not significant.

The comparison was made between 2*1 minute of tooth brushing and 5*20 min of chewing. These figures are chosen to simulate a realistic daily use of either toothbrush or chewing gum. It should be mentioned though that the chewing rate normally is 60 chew/min and the chewing machine only chews 22/min. This means a chewing time of only about 7 minutes!!

Some 40 minutes chews were done in order to compensate for the slow chewing frequency. This was obvious though, that doubling the chewing time not provide the same effect as a faster chewing frequency. Therefore it will not be possible to compare our results to the results former achieved by C. Kleber where the chewing was done at another machine and at a frequency of about 50 cycles/minute.

The ΔE max values in table 5 are not significant different which implies that the amount of stain available for removal was the same in the different groups.

In general there are considerable deviations in the results. The reason for that is not clear but it could be due to the spectrophotometer even though it was calibrated at the beginning of each day and sometimes during the day. Never the less the measured values occasionally was decreased after chewing another 20 min.

The L* values represents as mentioned the white in colour and a perfect white is 100. The graph above shows the measured L* values and it is obvious that more and more stain is removed as the chewing time is prolonged in the A gum but not with the placebo gum B. This means that the chewing itself is not effective enough to remove the stain.

The change in colour between chewing was obvious to the eye. C. Kleber has mentioned that a ΔE around 1 can be detected by the human eye.

Example 5

Study for Assessing Dental Plaque

The purpose of this human clinical study was to evaluate the potential for sugarless chewing gum containing zinc acetate to inhibit the formation of dental plaque on initially plaque-free tooth surfaces compared to conventional tooth brushing.

Study Design Summary

The test population consisted of 15 healthy adults who were known plaque-formers and regularly used chewing gum.

The clinical consisted of a randomized, double-blind, 3-way cross-over experimental design using a 2-day no-oral-hygiene plaque model. Adult subjects initially received a partial dental prophylaxis (no scaling or flossing) to remove all supragingival plaque. Then they were abstained for 2 days from all oral hygiene procedures other than the gum chewing or tooth brushing performed as a part of this study. Dental floss, toothpicks, mouthwashes, interdental stimulators, oral irrigation devices, and other commercial chewing gums and oral hygiene aids were not allowed during the trial periods. The 2-day no-oral-hygiene trial and 5-day washout periods occurred until all subjects had participated in each of the 3 treatment groups. The possibility of a carry-over effect from one test period to the next was minimized by requiring at least a 5-day washout period and by cleaning the participants' teeth before the start of each test period. In order to prevent a possible decrease in the plaque formation rates resulting from repeated dental cleanings, all plaque-free baselines were established by using rubber cup polishings with a standard dentifrice in lieu of a conventional dental prophylaxis with scaling and prophy paste. Also, no flossing was performed by the hygienists.

During each 2-day treatment period, the subjects assigned a chewing gum chewed 2 pieces of the gum for 10 minutes 5 times daily with no other oral hygiene. They also refrained from eating or drinking for 30 minutes after each chewing session in order to maximize the treatment effect. Those not assigned a gum brushed their teeth twice daily for 1 minute. After 2 days, each participant was checked for oral health and visually scored for plaque by an experienced dental examiner. The scoring occurred as close as possible to exactly 48 hours. Individual subjects were appointed and examined at the same time of day for each cross-over period. After the subjects had participated in each of the 3 cross-over periods, the plaque scores was tabulated and statistically compared by group.

Furthermore, plaque data for the various tooth surfaces were separately analyzed in order to determine the dental areas where the chewing gum was most effective.

Baseline Examinations

Before the start of each of the 2-day test periods, the subjects had all supragingival plaque removed from their teeth by a dental hygienist, because a plaque-free baseline will increase the likelihood of detecting the activity of the zinc salt since it functions predominately by inhibiting the formation of new plaque on enamel surfaces. If sufficient plaque develops, however, the chewing gums may also function by mechanically removing some of the deposits. Thus, a plaque-free baseline will minimize the mechanical cleaning effect of the chewing gums and maximize the effect of the added zinc salt.

The dental cleaning consisted of only a rubber cup polishing with dentifrice in order to remove all visible plaque from the facial and lingual tooth surfaces. No scaling, flossing, or use of prophy paste was allowed to establish the plaque-free baselines. This procedure was followed because repeated complete dental prophylaxes over relatively short periods of time in cross-over studies may cause a decrease in plaque formation rates. If a subject required a complete dental prophylaxis to remove stain and calculus, this was performed at the screening exam before the start of the study.

Treatments

After removal of all plaque, the subject was assigned to one of 3 treatment groups according to a balanced Latin Square design. The 3 test groups consisted of 2 differently flavored chewing gums containing 0.5 mg zinc acetate compared to tooth brushing alone. The chewing gum and brushing treatments was unsupervised during the 2-day test periods. The subjects chewed 2 tablets of their assigned gum 5 times per day for 10 minutes each time. The chewing sessions occurred (1) after breakfast; (2) after lunch; (3) mid-afternoon at 3 p.m.; (4) after dinner; and (5) before bedtime. Timers were provided so that each subject could monitor their 10-minute chewing sessions. To maximize treatment substantivity and exposure time, subjects was refrained from eating or drinking for 30 minutes following each chewing session. The participants returned their unused gum so that usage levels and compliance can be estimated.

Test Products

The chewing gums under evaluation were provided by Gumlink A/S, Denmark, in blank, coded packaging. The following products were tested:

(1) Flavored sugarless chewing gum A (table 1) containing 0.50 mg zinc acetate per piece with no tooth brushing.

(2) Flavored sugarless chewing gum C (table 1) containing 0.50 mg zinc acetate per piece with no tooth brushing (3) Tooth brushing with no chewing gum (control).

The chewing gums used in this study was prepared in accordance with Good Manufacturing Procedures (GMP) at the sponsor's Food Approved, ISO Standardized facility. The gums contained NutraSweet® and the standard warning to phenylketonurics was on the packaging.

Final Examinations

The final exam for each subject was scheduled at exactly 48 hours following their baseline exam. Subjects continued to follow the same 48-hour sequence for each of the 3 cross-over periods in order to minimize any effect arising from the time of day that the chewing gum was last used. After each 2-day trial period, the subjects were scored first for oral health and then for dental plaque in order to determine the amount of plaque that formed on the teeth. All exams and cleanings were performed by experienced, licensed dental personnel using accepted methods of infection control in compliance with OSHA's *Standard for Occupational Exposure to Bloodborne Pathogens* (29 CRF 1910.1930) and *Indiana Public Law* (123-1988). Sterile instruments, disposable rubber gloves, and procedural masks were used for each exam in order to protect both the dental staff and subjects from transmissible diseases.

The plaque was scored using the modified Quigley-Hein (MQH) plaque index. In order to facilitate scoring, the plaque was disclosed using a dye solution (Red Cote®, John O. Butler Company). Subjects rinsed with 5 ml of Red Cote® disclosant for 10 seconds, then expectorated and rinsed for 10 seconds with 10 ml of distilled water to remove the residual disclosant. Using a dental light and mouth mirror, the dental examiner visually scored the teeth for plaque deposits.

Scoring Methods

Oral Tissue Health

A visual inspection of the oral cavity using a standard dental light and mouth mirror were conducted at the screening and final examinations. The tissue structures checked included the buccal, labial and sublingual mucosa, gingivae, tongue, hard and soft palate, oropharynx, floor of the mouth, lips, and teeth. The site, size, and severity of any lesions or aberrations and tentative diagnosis, if possible, were recorded on the case report forms. A judgement were made as to whether or not the abnormalities were attributable to the test materials.

Modified Quigley-Hein (MQH) Plaque Index

Plaque deposits on the teeth were scored by an experienced examiner using the Quigley-Hein Index as modified by Turesky et al. (Turesky, S.; Gilmore, N.D.; and Glickman, I.: Reduced plaque formation by the chloromethyl analogue of Victamine C. *J Periodontol* 41:41-44, 1970). It is a numerical index based on plaque area that gives greater attention to the gingival third of the tooth in order to differentiate relatively subtle amounts of plaque. In order to obtain greater sensitivity, plaque removal from the proximal as well as gingival areas were quantified by dividing each tooth into six areas for scoring instead of just the two areas normally scored with the Turesky method (Deasy, M. J.; Singh, S. M.; Rustogi, K. N.; Petrone, D. M.; Battista, G.; Petrone, M. E.; and Volpe, A. R.: Effect of a dentifrice containing triclosan and a copolymer on plaque formation and gingivitis. *Clin Prev Dent* 13:12-19, 1991). Separate scores were measured for the marginal, mesial, and distal segments of both the facial and lingual surfaces of all teeth (except third molars) using the same criteria as the Turesky modification. The various surfaces of the teeth were assigned values as follows:

0=No visible plaque.

1=Separate flecks of plaque at the cervical margin of the tooth.

2=A thin, continuous band of plaque (up to 1 mm wide) at the cervical margin.

3=A band of plaque wider than 1 mm but covering less than one-third of crown.

4=Plaque covering at least one-third but less than two-thirds of crown.

5=Plaque covering two-thirds or more of crown.

An average plaque score per subject were calculated by summing the scores for all surfaces and dividing by the total number of surfaces scored.

Results

The results of the experiment clearly showed that for the subjects chewing a gum according to the present invention the formation of plaque was markedly reduced in comparison to the subject chewing the placebo gum. No side effects were observed during the study.

TABLE 6

Effect of zinc chewing gums on plaque formation during 2 days on no oral hygiene

| Group | Treatment[1] | N | MQH Scores (Mean ± SD) |
|---|---|---|---|
| 1 | Gum A | 15 | 2.60 ± 0.48 |
| 2 | Gum C | 15 | 2.38 ± 0.49 |
| 3 | Brushing | 15 | 1.61 ± 0.54 |

[1]Gums chewed 10 minutes, 5 times daily for 2 days with no other oral hygiene procedures. Toothbrushing performed for 1 minute 2 times daily.

TABLE 7

Effect of zinc chewing gums on plaque formation on facial/lingual tooth surface during 2 days of no oral hygiene

| | | MQH Plaque Score (Mean ± SD, N = 15)[2] | | |
|---|---|---|---|---|
| Jaw | Tooth Surface | Gum A | Gum C | Brushing |
| Maxilla | Facial | 3.61 ± 0.60 | 3.36 ± 0.81 | 1.87 ± 0.66 |
| | Lingual | 1.73 ± 0.66 | 1.60 ± 0.66 | 1.51 ± 0.71 |
| | All | 2.67 ± 0.49 | 2.43 ± 0.57 | 1.69 ± 0.59 |
| Mandible | Facial | 2.63 ± 0.75 | 2.49 ± 0.66 | 1.50 ± 0.67 |
| | Lingual | 2.42 ± 0.60 | 2.16 ± 0.44 | 1.58 ± 0.53 |
| | All | 2.53 ± 0.61 | 2.32 ± 0.48 | 1.54 ± 0.53 |
| Both | All | 2.60 ± 0.48 | 2.38 ± 0.49 | 1.61 ± 0.54 |

[2]Gums chewed 10 minutes, 5 times daily for 2 days with no other oral hygiene procedures. Toothbrushing performed for 1 minute 2 times daily

TABLE 8

Matched-pair group comparisons of plaque scores by facial/lingual tooth surface per jaw

| | Tooth | MQH Plaque Score (Mean ± SD, N = 15)[3] | | |
|---|---|---|---|---|
| Jaw | Surface | A-B | A-C | B-C |
| Maxilla | Facial | 0.36 ± 0.59* | 1.75 ± 0.81** | 1.39 ± 0.94** |
| | Lingual | 0.13 ± 0.35 | 0.23 ± 0.34* | 0.10 ± 0.43 |
| | All | 0.24 ± 0.31* | 0.99 ± 0.48** | 0.74 ± 0.59** |
| Mandible | Facial | 0.15 ± 0.45 | 1.13 ± 0.72** | 0.99 ± 0.74** |
| | Lingual | 0.26 ± 0.41* | 0.84 ± 0.54** | 0.58 ± 0.49** |
| | All | 0.20 ± 0.40 | 0.96 ± 0.59** | 0.78 ± 0.59** |
| Both | All | 0.22 ± 0.33* | 0.99 ± 0.48** | 0.77 ± 0.55** |

[3]Mean difference between groups ± standard deviation, n = 15
Code identification:
Group A = Chewing gum A
Group B = Chewing gum C
Group C = Toothbrushing
*Significantly different at $p < 0.05$
**Significantly different at $p < 0.001$ The gum formulation A seemed less effective in inhibiting plaque than gum formulation C. It is believed that this effect is caused by an undesired reaction between zinc and osteopontin in gum formulation A.

In the following other formulations of chewing gum are described. These formulations are also considered to be useful according to the present invention.

Formulation Example 2

| Ingredients | % by weight |
|---|---|
| Gum base | 39.5 |
| Sorbitol | 39.99 |
| Glycerine | 5 |
| Green tea | 4 |
| Flavour | 2.7 |
| Craneberry | 2.7 |
| Dicalcium phosphate | 2.5 |
| Talc | 2.5 |
| Lecithine | 0.2 |
| Zinc acetate | 0.5 |
| Acesulfane K | 0.2 |
| Aspartame | 0.2 |
| *Aloe vera* | 0.01 |

Formulation Example 3

| Ingredients | % by weight |
|---|---|
| Gum base | 50 |
| Sorbitol | 34.98 |
| flavour | 3 |
| calcium carbonate | 4 |
| *eucalyptus* | 3 |
| xylitol | 4.6 |
| Acesulfane K | 0.2 |
| Aspartame | 0.2 |
| *Aloe vera* | 0.01 |
| Dicalcium phosphate | 0.01 |

Formulation Example 4

| Ingredients | % by weight |
|---|---|
| Gum base | 45 |
| Sorbitol | 29.99 |
| xylitol | 10 |
| Maltitol syrup | 5 |
| Glycerin | 2 |
| Flavour | 2 |
| *Aloe vera* | 1.5 |
| Baking soda | 1.5 |
| Champex | 1.5 |
| Black seaweed | 0.9 |
| Acesulfane K | 0.3 |
| Aspartame | 0.3 |
| Dicalcium phosphate | 0.01 |

Formulation Example 5

| Ingredients | % by weight |
|---|---|
| Gum base | 39.5 |
| Sorbitol | 39.98 |
| Glycerine | 5 |
| Green tea extract | 3.9 |
| Flavour | 2.5 |
| Grape seed | 3 |
| Calcium carbonate | 3.5 |
| Talc | 1.5 |
| Lecithine | 0.2 |
| Zinc acetate | 0.5 |
| Acesulfane K | 0.2 |

Formulation Example 6

| Ingredients | % by weight |
| --- | --- |
| Gum base | 40 |
| Sorbitol | 30.31 |
| Maltitol syrup | 5 |
| Lecithine | 0.2 |
| Green tea extrakt | 1.5 |
| *Aronia* | 2 |
| Zink acetate | 0.06 |
| Sodium fluoride | 0.03 |
| NaHCO$_3$ | 1 |
| Calcium carbonat | 3 |
| Dicalcium phosphat | 3 |
| Calcium pyrophosphat | 6.7 |
| Titandioxid | 1 |
| Thyme | 0.5 |
| Acesulfame | 0.2 |
| Aspartame | 0.2 |
| Flavour | 1.3 |
| *Eucalyptus* | 1 |
| Xylitol | 5 |

Formulation Example 7

| Ingredients | % by weight |
| --- | --- |
| Gum base | 40 |
| Sorbitol | 42.07 |
| Maltitol syrup | 5 |
| Lecithine | 0.2 |
| Calcium carbonat | 4 |
| Sodium fluoride | 0.03 |
| *Aronia* | 3 |
| Green tea extrakt | 3 |
| Osteopontin | 0.5 |
| Vitamin C | 0.5 |
| Acesulfame | 0.2 |
| Aspartame | 0.2 |
| Flavour | 1.3 |

Formulation Example 8

| Ingredients | % by weight |
| --- | --- |
| Gum base | 40 |
| Sorbitol | 44.37 |
| Maltitol syrup | 5 |
| Lecithine | 0.2 |
| NaHCO$_3$ | 1 |
| Sodium fluoride | 0.03 |
| *Aronia* | 3 |
| Green tea extrakt | 3 |
| Osteopontin | 0.5 |
| Vitamin C | 0.5 |

-continued

| Ingredients | % by weight |
| --- | --- |
| Acesulfame | 0.2 |
| Aspartame | 0.2 |
| Flavour | 2 |

Formulation Example 9

| Ingredients | % by weight |
| --- | --- |
| Gum base | 40 |
| Sorbitol | 37.17 |
| Maltitol syrup | 5 |
| Lecithine | 0.2 |
| Calcium pyrophosphat | 7 |
| Sodium fluoride | 0.03 |
| *Aronia* | 3 |
| Green tea extrakt | 3 |
| Osteopontin | 0.5 |
| Vitamin C | 0.5 |
| Acesulfame | 0.3 |
| Aspartame | 0.3 |
| Flavour | 3 |

Formulation Example 10

| Ingredients | % by weight |
| --- | --- |
| Gum base | 40 |
| Sorbitol | 33.97 |
| Maltitol syrup | 5 |
| Calcium carbonat | 3 |
| Calcium pyrophospate | 7 |
| Sodium fluoride | 0.03 |
| *Aronia* | 3 |
| Green tea extrakt | 3 |
| Osteopontin | 0.5 |
| Vitamin C | 0.5 |
| NaHCO$_3$ | 1 |
| Acesulfame | 0.25 |
| Aspartame | 0.25 |
| Flavour | 2.5 |

Formulation Example 11

| Ingredients | % by weight |
| --- | --- |
| Gum base | 40 |
| Sorbitol | 38.9 |
| Maltitol syrup | 5 |
| Lecithine | 0.2 |
| Calcium carbonat | 4 |
| Dicalcium phosphate | 2.5 |
| Acesulfame | 0.2 |
| Aspartame | 0.2 |
| Flavour | 2 |
| *Aronia* | 3 |
| Green tea extrakt | 3 |
| Osteopontin | 0.5 |
| Vitamin C | 0.5 |

-continued

| Ingredients | % by weight |
| --- | --- |
| Aspartame | 0.2 |
| Dicalcium phosphate | 0.01 |
| *Aloe vera* | 0.01 |

Formulation Example 12

| Ingredients | % by weight |
|---|---|
| Gum base | 40 |
| Sorbitol | 37.17 |
| Maltitol syrup | 5 |
| Lecithine | 0.2 |
| Calcium carbonat | 4 |
| Dicalcium phosphate | 2.5 |
| Acesulfame | 0.3 |
| Aspartame | 0.3 |
| Flavour | 3.5 |
| *Aronia* | 3 |
| Green tea extrakt | 3 |
| Osteopontin | 0.5 |
| Vitamin C | 0.5 |
| Sodium fluoride | 0.03 |

Formulation Example 13

| Ingredients | % by weight |
|---|---|
| Gum base | 40 |
| Sorbitol | 33.37 |
| Maltitol syrup | 5 |
| Lecithine | 0.2 |
| Acesulfame | 0.2 |
| Aspartame | 0.2 |
| Flavour | 2 |
| Green tea extrakt | 3 |
| Dicalcium phosphate | 2.5 |
| *Aronia* | 3 |
| Xylitol | 5 |
| Immuglobuline-lysozyme | 5 |
| Vitamin C | 0.5 |
| Sodium fluoride | 0.03 |

Formulation Example 14

| Ingredients | % by weight |
|---|---|
| Gum base | 45 |
| Sorbitol | 41.17 |
| Maltitol syrup | 5 |
| Acesulfame | 0.3 |
| Aspartame | 0.3 |
| Flavour | 4 |
| Lecithine | 0.2 |
| NaHCO$_3$ | 1 |
| Sodium fluoride | 0.03 |
| Green tea extrakt | 2 |
| Osteopontin | 0.5 |
| Vitamin C | 0.5 |

Formulation Example 15

| Ingredients | % by weight |
|---|---|
| Gum base | 45 |
| Sorbitol | 41.67 |
| Maltitol syrup | 5 |
| Lecithine | 0.2 |
| *Eucaluptus* | 1.5 |
| NaHCO$_3$ | 0.03 |
| Zinc carbamate | 0.5 |
| Dicalcium phosphat | 3 |
| Osteopontin | 0.5 |
| Acesulfame | 0.2 |
| Aspartame | 0.2 |
| Flavour | 2.2 |

Formulation Example 16

| Ingredients | % by weight |
|---|---|
| Gum base | 45 |
| Sorbitol | 32.57 |
| Maltitol syrup | 5 |
| Lecithine | 0.2 |
| *Eucaluptus* | 1.5 |
| NaHCO$_3$ | 0.03 |
| Zinc benzoate | 0.5 |
| Dicalcium phosphate | 3 |
| Osteopontin | 0.5 |
| Acesulfame | 0.3 |
| Aspartame | 0.3 |
| Flavour | 2.6 |
| Green tea extract | 2 |
| Thymol | 0.5 |
| Xylitol | 4 |
| *Aronia* | 2 |

The various embodiments mentioned in the above description are non-limiting examples of the present invention. Other examples can be based by combination of the various figures, features and agents within the scope of the following claims.

The invention claimed is:

1. A compressed chewing gum tablet comprising:
   at least gum base;
   at least one whitening agent;
   at least one fresh-breath agent;
   at least one anti-plaque agent;
   at least one anti-gingivitis agent; and
   at least one re-mineralization agent,
   wherein said compressed chewing gum tablet is made from a compressed mixture of granules and agents, and wherein when said compressed chewing gum tablet is chewed for at least 5 minutes it provides a whitening effect, a fresh-breath effect, an anti-plaque effect, an anti-gingivitis effect and a re-mineralization effect that is at least 50% of what would be obtained by brushing with a toothbrush for 2 minutes.

2. A compressed chewing gum tablet according to claim 1, wherein the tablet comprises two or more layers.

3. A compressed chewing gum tablet according to claim 2, wherein at least one of the layers is substantially free of gum base.

4. A compressed chewing gum tablet according to claim 2, wherein at least one of said agents is present in the tablet in only one of the layers.

5. A compressed chewing gum tablet according to claim 2, wherein at least one of said agents located in the tablet in two of the layers is not present in all layers.

6. A compressed chewing gum tablet according to claim 2, wherein the tablet comprises at least one barrier layer.

7. A compressed chewing gum tablet according to claim 1, wherein the tablet is coated.

8. A compressed chewing gum tablet according to claim 1, wherein at least one of said agents is present in the coating.

9. A compressed chewing gum tablet according to claim 1, wherein the granules comprise gum base granules.

10. A compressed chewing gum tablet according to claim 1, wherein the granules comprise chewing gum powder.

11. A compressed chewing gum tablet according to claim 1, wherein at least one of said agents is present only in a fraction of the granules, and at least a second of said agents is present only in another fraction of the granules.

12. A compressed chewing gum tablet according to claim 1, further comprising at least one chewing gum ingredient selected from sweeteners and/or flavours.

13. A compressed chewing gum tablet according to claim 1, wherein the gum base constitutes at least 35 weight-% of the tablet.

14. A compressed chewing gum tablet according to claim 13, wherein the gum base constitutes at least 37 weight-% of the tablet.

15. A compressed chewing gum tablet according to claim 13, wherein the gum base constitutes at least 9 weight % of the tablet.

16. A compressed chewing gum tablet according to claim 1, wherein the gum base constitutes 60-100% of the granules.

17. A compressed chewing gum tablet according to claim 1, wherein at least one of the agents is present in the granules and mixed into the gum base.

18. A compressed chewing gum tablet according to claim 1, wherein a first fraction of the granules comprises at least one agent, and a second fraction of the granules comprises at least one agent and the at least one agent comprised in the first fraction is different from the at least one agent comprised in the second fraction.

19. A compressed chewing gum tablet according to claim 1, further comprising at least one anti-calculus agent.

20. A compressed chewing gum tablet according to claim 1, wherein the chewing gum when chewed on a daily basis as a toothbrush substitute provides
  a) a whitening effect corresponding to at least 50% of the whitening effect of daily brushing of teeth with a new toothbrush,
  b) a fresh-breath effect corresponding to at least 100% of the fresh-breath effect of daily brushing of teeth with a new toothbrush,
  c) an anti-plaque effect corresponding to at least 60% of the anti-plaque effect of daily brushing of teeth with a new toothbrush,
  d) an anti-gingivitis effect corresponding to at least 65%of the anti-gingivitis effect of daily brushing of teeth with a new toothbrush,
  e) optionally a re-mineralization effect corresponding to at least 65% of the re-mineralization effect of daily brushing of teeth with a new toothbrush,
  f) optionally an anti-calculus effect corresponding to at least 25% of the anti-calculus effect of daily brushing of teeth with a new toothbrush, and providing a substantially lower abrasive effect than the abrasive effect caused by daily brushing of teeth with a new toothbrush.

21. A compressed chewing gum tablet according to claim 1, wherein the gum base constitutes 70-100 weight % of the granules.

22. A compressed chewing gum tablet according to claim 1, wherein the gum base constitutes 85-100 weight % of the granules.

23. A compressed chewing gum tablet, comprising
  at least gum base;
  at least one whitening agent;
  at least one fresh-breath agent;
  at least one anti-plaque agent;
  at least one anti-gingivitis agent; and
  at least one re-mineralization agent,
  wherein said compressed chewing gum tablet is made from a compressed mixture of granules and agents, and
  wherein said compressed chewing gum tablet when chewed for at least 5 minutes provides a whitening effect, a fresh-breath effect, an anti-plaque effect, an anti-gingivitis effect and a re-mineralization effect that is at least 50% of what would be obtained by brushing with a toothbrush for 2 minutes.

24. A compressed chewing gum tablet which comprises:
  at least gum base;
  at least one whitening agent;
  at least one fresh-breath agent;
  at least one anti-plaque agent;
  at least one anti-gingivitis agent;
  at least one re-mineralization agent,
  wherein said compressed chewing gum tablet is made from a compressed mixture of granules and agents, wherein the tablet comprises two or more layers, and wherein the gum base constitutes at least 35 weight-% of the tablet, and
  wherein said tooth brushing substitute formed as a compressed tablet is formed such that chewing said compressed chewing gum tablet for at least 5 minutes provides a whitening effect, a fresh-breath effect, an anti-plaque effect, an anti-gingivitis effect and a re-mineralization effect that is at least 50% of what would be obtained by brushing with a toothbrush for 2 minutes.

25. A tooth brushing substitute formed as a compressed chewing gum tablet according to claim 24, further comprising at least one anti-calculus agent.

26. A compressed chewing gum tablet which comprises:
  at least gum base and
  a) at least one whitening agent,
  b) at least one fresh-breath agent,
  c) at least one anti-plaque agent,
  d) at least one anti-gingivitis agent,
  e) at least one re-mineralization agent, and f) optionally at least one anti-calculus agent, wherein said compressed chewing gum tablet is made from a compressed mixture of granules and agents, wherein gum base constitutes from 60 to 100% of the granules, and
  wherein chewing said compressed chewing gum tablet for at least 5 minutes provides a whitening effect, a fresh-breath effect, an anti-plaque effect, an anti-gingivitis effect and a re-mineralization effect that is at least 50% of what would be obtained by brushing with a toothbrush for 2 minutes.

27. A tooth brushing substitute formed as a compressed chewing gum tablet according to claim 26, further comprising at least one anti-calculus agent.

* * * * *